United States Patent [19]
Croteau et al.

[11] Patent Number: 5,871,988
[45] Date of Patent: Feb. 16, 1999

[54] **DNA ENCODING LIMONENE SYNTHASE FROM *MENTHA SPICATA***

[75] Inventors: Rodney B. Croteau, Pullman, Wash.; Shelia M. Colby, Berkeley, Calif.

[73] Assignee: Washington State University Research Foundation, Pullman, Wash.

[21] Appl. No.: 846,526

[22] Filed: Apr. 29, 1997

Related U.S. Application Data

[63] Continuation of Ser. No. 582,802, Jan. 4, 1996, abandoned, which is a continuation of Ser. No. 145,941, Oct. 28, 1993, abandoned.

[51] Int. Cl.$^6$ .............................. C12N 9/00; C12N 15/63; C12P 21/02; C07H 21/04
[52] U.S. Cl. ..................... 435/183; 435/69.1; 435/252.3; 435/320.1; 536/23.2
[58] Field of Search .......................... 536/23.2; 435/183, 435/252.3, 320.1, 69.1

[56] References Cited

PUBLICATIONS

Kang, M.H. et al. "Isolation of a genomic clone for cytochrome P450 oxidase from *Mentha piperita*" Molecules and Cells (Sep. 1993), vol. 3, No. 3, pp. 283–288.

Song, S.I. et al. "Molecular cloning and nucleotide sequencing of cDNA encoding the precursor for soybean trypsin inhibitor (Kunitz type)" Molecules and Cells (1991), vol. 1, No. 3, pp. 317–324, abstract only.

Lohman, K.N. "Floral induction in *Pharbitis nil, Perilla crispa*, and *Arabidopsis thaliana*" Dissertation Abstracts International (1992), vol. 53, No. 6B, p. 2691, abstract only.

The New Royal Horticultural Society Dictionary of Gardening. Edited by A. Huxley et al. London: Macmillan Press, 1992, p. 525.

Bailey, L.H. The Standard Cyclopedia of Horticulture. New York: Macmillan Company, 1935, p. 2553.

John, M.E. "An efficient method for isolation of RNA and DNA from plants containing polyphenolics" Nucleic Acids Research (May, 1992), vol. 20, No. 9, p. 2381.

Alberts, B. et al. "Molecular Biology of the Cell" published 1989 by Garland Publishing Inc. (N.Y.), pp. 262–263.

Alberts, B. et al. (1989) *Molecular Biology of the Cell* Second Ed. Garland Publishing Inc., New York. pp. 185–187 and 265–266.

Colby, S.M., Alonso, W.R., Croteau, R. (1992) "Isolation and characterization of cDNA encoding limonene cyclase in spearmint" J. Cell Biochem. Suppl. 0 vol. 16, Part F p. 230.

*Primary Examiner*—Robert A. Wax
*Assistant Examiner*—Kawai Lau
*Attorney, Agent, or Firm*—Christensen O'Connor Johnson & Kindness PLLC

[57] ABSTRACT cDNA encoding (–)-4S-limonene synthase from spearmint has been isolated and sequenced, and the corresponding amino acid sequence has been determined. Accordingly, isolated DNA sequences are provided which code for the expression of limonene synthase, such as the sequence designated SEQ ID No:11 which encodes limonene synthase from spearmint (*Mentha spicata*). In other aspects, replicable recombinant cloning vehicles are provided which code for limonene synthase or for a base sequence sufficiently complementary to at least a portion of the limonene synthase DNA or RNA to enable hybridization therewith (e.g., antisense limonene synthase RNA or fragments of complementary limonene synthase DNA which are useful as polymerase chain reaction primers or as probes for limonene synthase or related genes). In yet other aspects, modified host cells are provided that have been transformed, transfected, infected and/or injected with a recombinant cloning vehicle and/or DNA sequence encoding limonene synthase. Thus, systems and methods are provided for the recombinant expression of limonene synthase that may be used to facilitate the production, isolation and purification of significant quantities of recombinant limonene synthase (or of the primary enzyme product, limonene) for subsequent use, to obtain expression or enhanced expression of limonene synthase in plants to attain enhanced limonene production as a predator defense mechanism, or may be otherwise employed for the regulation or expression of limonene synthase or the production of limonene.

10 Claims, 9 Drawing Sheets

CNBr #1 (99-119)
20 mer
128 oligonucleotides

```
E L E K E T D Q I R  Q L E L I D D L Q R M
      GAAAAAGAAACAGATCAGAT
           G G G C  A
             G      T
                    C
```

*Fig. 2A.*

CNBr #2 (273-299)
23 mer
48 oligonucleotides

```
                        V8 #1 (284-299)
N P V V L E L A I L D  L N I V Q A Q F Q E E L K E S F
                         AATATTGTICAAGCICAATTTCA
                              C C   G    G G C
                                         A
```

*Fig. 2B.*

CNBr #3 (342-361)
17 mer
48 oligonucleotides

```
G K V N A L I T V I  K D I Y D V Y G T L
                     AAGGATATTACGATGT
                       A   C C T C
                                A
```

*Fig. 2C.*

```
pLC5.2                          AGAGAGAGAGAGGAAGGAAAGATTAATC         28
pLC4.1                          gagag---a------c------------
pLC8.5          attaatcctagaaaaacat---a------c------------ pLC5.2   ATGGCTCTCAAAGTGTTAAGTGTTGCAACTCAAATGGCGATTCCTAGCAA         78
pLC4.1   --------------------------------------------------
pLC8.5   --------------------------------------------------
          M   A   L   K   V   L   S   V   A   T   Q   M   A   I   P   S   N    17 pLC5.2   CCTAACGACATGTCTTCAACCCTCACACTTCAAATCTTCTCCAAAACTGT        128
pLC4.1   --------------------------------------------------
pLC8.5   --------------------------------------------------
          L   T   T   C   L   Q   P   S   H   F   K   S   S   P   K   L   L    34 pLC5.2   TATCTAGCACTAACAGTAGTAGTCGGTCTCGCCTCCGTGTGTATTGCTCC        178
pLC4.1   ----------------------
pLC8.5   ----------------------
pLC10.1        c-----------------a-----------------------t----
          S   S   T   N   S   S   S   R   S   R   L   R   V   Y   C   S        50 pLC5.2   TCCTCGCAACTCACTACTGAAAGACGATCCGGAAACTACAACCCTTCTCG        228
pLC10.1  --------------------------------------------------
          S   S   Q   L   T   T   E   R   R   S   G   N   Y   N   P   S   R    67 pLC5.2   TTGGGATGTCAACTTCATCCAATCGCTTCTCAGTGACTATAAGGAGGACA        278
pLC10.1  -----------------------g--------------------------
          W   D   V   N   F   I   Q   S   L   L   S   D   Y   K   E   D   K    84 pLC5.2   AACACGTGATTAGGGCTTCTGAGCTGGTCACTTTGGTGAAGATGGAACTG        328
pLC10.1  -------
           H   V   I   R   A   S   E   L   V   T   L   V   K   M   E   L       100 pLC5.2   GAGAAAGAAACGGATCAAATTCGACAACTTGAGTTGATCGATGACTTGCA        378
          E   K   E   T   D   Q   I   R   Q   L   E   L   I   D   D   L   Q    117 pLC5.2   GAGGATGGGGCTGTCCGATCATTTCCAAAATGAGTTCAAAGAAATCTTGT        428
          R   M   G   L   S   D   H   F   Q   N   E   F   K   E   I   L   S    134 pLC5.2   CCTCTATATATCTCGACCATCACTATTACAAGAACCCTTTTCCAAAAGAA        478
              S   I   Y   L   D   H   H   Y   Y   K   N   P   F   P   K   E    150 pLC5.2   GAAAGGGATCTCTACTCCACATCTCTTGCATTTAGGCTCCTCAGAGAACA        528
          E   R   D   L   Y   S   T   S   L   A   F   R   L   L   R   E   H    167 pLC5.2   TGGTTTTCAAGTCGCACAAGAGGTATTCGATAGTTTCAAGAACGAGGAGG        578
              G   F   Q   V   A   Q   E   V   F   D   S   F   K   N   E   E   G  184 pLC5.2   GTGAGTTCAAAGAAAGCCTTAGCGACGACACCAGAGGATTGTTGCAACTG        628
              E   F   K   E   S   L   S   D   D   T   R   G   L   L   Q   L    200 pLC5.2   TATGAAGCTTCCTTTCTGTTGACGGAAGGCGAAACCACGCTCGAGTCAGC        678
          Y   E   A   S   F   L   L   T   E   G   E   T   T   L   E   S   A    217
```

*Fig. 4A.*

| | | |
|---|---|---|
| pLC5.2 | GAGGGAATTCGCCACCAAATTTTTGGAGGAAAAAGTGAACGAGGGTGGTG | 728 |
| | R E F A T K F L E E K V N E G G V | 234 |
| pLC5.2 | TTGATGGCGACCTTTTAACAAGAATCGCATATTCTTTGGACATCCCTCTT | 778 |
| | D G D L L T R I A Y S L D I P L | 250 |
| pLC5.2 | CATTGGAGGATTAAAAGGCCAAATGCACCTGTGTGGATCGAATGGTATAG | 828 |
| | H W R I K R P N A P V W I E W Y R | 267 |
| pLC5.2 | GAAGAGGCCCGACATGAATCCAGTAGTGTTGGAGCTTGCCATACTCGACT | 878 |
| | K R P D M <u>N P V V L E L A I L D L</u> | 284 |
| pLC5.2 | TAAATATTGTTCAAGCACAATTTCAAGAAGAGCTCAAAGAATCCTTCAGG | 928 |
| | <u>N I V Q A Q F Q E E L K E S F R</u> | 300 |
| pLC5.2 | TGGTGGAGAAATACTGGGTTTGTTGAGAAGCTGCCCTTCGCAAGGGATAG | 978 |
| | W W R N T G F V E K L P F A R D R | 317 |
| pLC5.2 | ACTGGTGGAATGCTACTTTTGGAATACTGGGATCATCGAGCCACGTCAGC | 1028 |
| | L V E C Y F W N T G I I E P R Q H | 334 |
| pLC5.2 | ATGCAAGTGCAAGGATAATGATGGGCAAAGTCAACGCTCTGATTACGGTG | 1078 |
| | A S A R I M M <u>G K V N A L I T V</u> | 350 |
| pLC5.2 | ATCGATGATATTTATGATGTCTATGGCACCTTAGAAGAACTCGAACAATT | 1128 |
| | <u>I D D I Y D V Y G T L E E L E Q F</u> | 367 |
| pLC5.2 | CACTGACCTCATTCGAAGATGGGATATAAACTCAATCGACCAACTTCCCG | 1178 |
| | T D L I R R W D I N S I D Q L P D | 384 |
| pLC5.2 | ATTACATGCAACTGTGCTTTCTTGCACTCAACAACTTCGTCGATGATACA | 1228 |
| | Y M Q L C F L A L N N F V D D T | 400 |
| pLC5.2 | TCGTACGATGTTATGAAGGAGAAAGGCGTCAACGTTATACCCTACCTGCG | 1278 |
| | S Y D V M K E K G V N V I P Y L R | 417 |
| pLC5.2 | GCAATCGTGGGTTGATTTGGCGGATAAGTATATGGTAGAGGCACGGTGGT | 1328 |
| | Q S W V D L A D K Y M V E A R W F | 434 |
| pLC5.2 | TCTACGGCGGGCACAAACCAAGTTTGGAAGAGTATTTGGAGAACTCATGG | 1378 |
| | Y G G H K P S L E E Y L E N S W | 450 |
| pLC5.2 | CAGTCGATAAGTGGGCCCTGTATGTTAACGCACATATTCTTCCGAGTAAC | 1428 |
| | Q S I S G P C M L T H I F F R V T | 467 |
| pLC5.2 | AGATTCGTTCACAAAGGAGACCGTCGACAGTTTGTACAAATACCACGATT | 1478 |
| | D S F T K E T V D S L Y K Y H D L | 484 |
| pLC5.2 | TAGTTCGTTGGTCATCCTTCGTTCTGCGGCTTGCTGATGATTTGGGAACC | 1528 |
| | V R W S S F V L R L A D D L G T | 500 |

*Fig. 4B.*

| | | |
|---|---|---|
| pLC5.2 | TCGGTGGAAGAGGTGAGCAGAGGGGATGTGCCGAAATCACTTCAGTGCTA | 1578 |
| | S  V  E  E  V  S  R  G  D  V  P  K  S  L  Q  C  Y | 517 |
| pLC5.2 | CATGAGTGACTACAATGCATCGGAGGCGGAGGCGCGGAAGCACGTGAAAT | 1628 |
| | M  S  D  Y  N  A  S  E  A  E  A  R  K  H  V  K  W | 534 |
| pLC5.2 | GGCTGATAGCGGAGGTGTGGAAGAAGATGAATGCGGAGAGGGTGTCGAAG | 1678 |
| | L  I  A  E  V  W  K  K  M  N  A  E  R  V  S  K | 550 |
| pLC5.2 | GATTCTCCATTCGGCAAAGATTTTATAGGATGTGCAGTTGATTTAGGAAG | 1728 |
| | D  S  P  F  G  K  D  F  I  G  C  A  V  D  L  G  R | 567 |
| pLC5.2 | GATGGCGCAGTTGATGTACCATAATGGAGATGGGCACGGCACACAACACC | 1778 |
| | M  A  Q  L  M  Y  H  N  G  D  G  H  G  T  Q  H  P | 584 |
| pLC5.2 | CTATTATACATCAACAAATGACCAGAACCTTATTCGAGCCCTTTGCATGA | 1828 |
| | I  I  H  Q  Q  M  T  R  T  L  F  E  P  F  A  * | 599 |
| pLC5.2 | GAGATGATGACGAGCCATCGTTTACTTACTTAAATTCTACCAAAGTTTTT | 1878 |
| pLC5.2 | CGAAGGCATAGTTCGTAATTTTTCAAGCACCAATAAATAAGGAGAATCGG | 1928 |
| pLC5.2 | CTCAAACAAACGTGGCATTTGCCACCACGTGAGCACAAGGGAGAGTCTGT | 1978 |
| pLC5.2 | CGTCGTTTATGGATGAACTATTCAATTTTTATGCATGTAATAATTAAGTT | 2028 |
| pLC5.2 | CAAGTTCAAGAGCCTTCTGCATATTTAACTATGTATTTGAATTTATCGAG | 2078 |
| pLC5.2 | TGTGATTTTCTGTCTTTGGCAACATATATTTTTGTCATATGTGGCATCTT | 2128 |
| pLC5.2 | ATTATGATATCATACAGTGTTTATGGATGATATGATACTATCAAAAAAAA | 2178 |
| pLC5.2 | AAAA | 2182 |

*Fig. 4C.*

```
Castor Bean    1 MALPSAAMQSNPEKLNLFHRLSSLPTTSLEYGN.NRFPFFSSSAKSHFKK  49
                 |. .. ..:.          :.|   ||:|: ::  .. | : ||..|  :.
Spearmint      1 .......MALKVLSVATQMAIPSNLTTCLQPSHFKSSPKLLSSTNSSSRS  43

Castor Bean   50 PTQACLSSTTHQEVRPLAYFPPTVWGNRFASLTFNPSEFESYDERVIVLK  99
                 . ..: ||.    . |. : : |. |: .|    :.. .. .  |. |
Spearmint     44 RLRVYCSSSQLTTERRSGNYNPSRWDVNFIQSLLSDYKEDKHVIRASELV  93

*
Castor Bean  100 KKVKDILISSTSDSVETVILIDLLCRLGVSYHFENDIEELLSKIFNSQ.. 147
                 . || : :....|  :  :  ||| | |:|:| ||:|::.:||.|: ..:
Spearmint     94 TLVK.MELEKETDQIRQLELIDDLQRMGLSDHFQNEFKEILSSIYLDHHY 142
                    | |..: .    |:|||  ::|:|:| ||:.|:.||| . || ::
Tobacco        1 .....MLLATGRKLADTLNLIDIIERLGISYHFEKEIDEILDQIYNQN.. 43

*
Castor Bean  148 .PDLVDEKECDLYTAAIVFRVFRQHGFKMSSDVFSKFKDSDGKFKESLRG 196
                  .: ....|  |||....|.||::|:|||.:.  :||..||:.:|.||||.:
Spearmint    143 YKNPFPKEERDLYSTSLAFRLLREHGFQVAQEVFDSFKNEEGEFKESLSD 192
                 .|       .||:...|.||||||:|||.:...|:|..|.:|:|.||||..
Tobacco       44 .SN.....CNDLCTSALQFRLLRQHGFNISPEIFSKFQDENGKFKESLAS  87

Castor Bean  197 DAKGMLSLFEASHLSVHGEDILEEAFAFTKDYLQSSAVE..LFPNLKRHI 244
                 |.:|:| |:|||  | ..||..||.| .|...:|:... |    : ..|  :|
Spearmint    193 DTRGLLQLYEASFLLTEGETTLESAREFATKFLEEKVNEGGVDGDLLTRI 242
                 |.  |||.|||||  :  |.::..||.|  .|.| ||. .   :.:.|  ...:
Tobacco       88 DVLGLLNLYEASHVRTHADDILEDALAFSTIHLESAAPH..LKSPLREQV 135

*
Castor Bean  245 TNALEQPFHSGVPRLEARKFIDLYEADIECRNETLLEFAKLDYNRVQLLH 294
                 .  .|: |:|. :.| :|. :|::|     : .|...:||:| ||.|  ||
Spearmint    243 AYSLDIPLHWRIKRPNAPVWIEWYRKRPD.MNPVVLELAILDLNIVQAQF 291
                 ...|:  .||. :.|.:....:|...  ..:  .| |:| :| ||:|::|
Tobacco      136 THALEQCLHKGVPRVETRFFISSIYDKEQSKNNVLLRFAKLDFNLLQMLH 185

Castor Bean  295 QQELCQFSKWWKDLNLASDIPYARDRMAEIFFWAVAMYFEPDYAHTRMII 344
                 |:|| :    :||::  .:....:|:||||:.|.:||..::.   ...:|  .|:::
Spearmint    292 QEELKESFRWWRNTGFVEKLPFARDRLVECYFWNTGIIEPRQHASARIMM 341
                 .:|| :    |||::  :||..||:|||||:||||||. |:.  ..|..  ||:|
Tobacco      186 KQELAQVSRWWKDLDFVTTLPYARDRVVECYFWALGVYFEPQYSQARVML 235

Castor Bean  345 AKVVLLISLIDDTIDAYATMEETHILAEAVARWDMSCLEKLPDYMKVIYK 394
                 :||   ||.:|||..|.|:|:|:||  . :..:  :  |||:.::::.||||.:.:
Spearmint    342 GKVNALITVIDDIYDVYGTLEELEQFTDLIRRWDINSIDQLPDYMQLCFL 391
                 .|.  ..:|.::|||..:|.|||:.|||.:|| |.|||||.||.|||||.:::
Tobacco      236 VKTISMISIVDDTFDAYGTVKELEAYTDAIQRWDINEIDRLPDYMKISYK 285
```

*Fig. 6A.*

```
Castor Bean 395 LLLNTFSEFEKELTAEGKSYSVKYGREAFQELVRGYYLEAVWRDEGKIPS 444
                | |  ..: . ::  |       :.| |:.: :|.  |  :|| |  :|.  ||
Spearmint   392 ALNNFVDDTSYDVMKEKGVNVIPYLRQSWVDLADKYMVEARWFYGGHKPS 441
                |: ::  .| . ::  ..   :::..  :.   ::. .|  ||. ||.:|..|.
Tobacco     286 AILDLYKDYEKELSSAGRSHIVCHAIERMKEVVRNYNVESTWFIEGYMPP 335

Castor Bean 445 FDDYLYNGSMTTGLPLVSTASFMGVQEITGLNEFQWLETNPKLSYASGAF 494
                :::|| |:. ...: | : | |: | : . :...:.| . ..|   |: .
Spearmint   442 LEEYLENSWQSISGPCMLTHIFFRVTDSFTKETVDSLYKYHDLVRWSSFV 491
                :.|||.|.:....  :: |  :: :... . :...:.| | ..:: | ::
Tobacco     336 VSEYLSNALATTTYYYLATTSYLGMKSATE.QDFEWLSKNPKILEASVII 384

*
Castor Bean 495 IRLVNDLTSHVTEQQRGHVASCIDCYMNQHGVSKDEAVKILQKMATDCWK 544
                :||.:||..  |.|   ||.|:.:::|||..:...|..|| | :..: ..:.||
Spearmint   492 LRLADDLGTSVEEVSRGDVPKSLQCYMSDYNASEAEARKHVKWLIAEVWK 541
                |:  || :|   |  |||:::.:::|:|.||. |. ||.  ...  :  ...||
Tobacco     385 CRVIDDTATYEVEKSRGQIATGIECCMRDYGISTKEAMAKFQNMAETAWK 434

Castor Bean 545 EINEECM.RQSQVSVGHLMRIVNLARLTDVSYKYG.DGYTDSQQ.LKQFV 591
                .:|.|  :  ::|..:  : :         |:|:|:..::    |  .. ||... :. :.| :
Spearmint   542 KMNAERVSKDSPFGKDFIGCAVDLGRMAQLMY.HNGDGHGTQHPIIHQQM 590
                .:|.:  :  :  ...|..:.:|:..   ::|:|:.::   |   ||  ||..  ....::...::
Tobacco     435 DINEGLL.RPTPVSTEFLTPILNLARIVEVTYIHNLDGYTHPEKVLKPHI 483

Castor Bean 592 KGLFVDPISI     601
                 .  :.:|:.
Spearmint   591 TRTLFEPFA .    599
                 ..  |.:.:
Tobacco     484 INLLVDSIKI     493
```

Fig. 6B.

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

```
Glu  Leu  Glu  Lys  Glu  Thr  Asp  Gln  Ile  Arg  Gln  Leu  Glu  Leu  Ile  Asp
1                   5                        10                       15
Asp  Leu  Gln  Arg  Met
                    20
```

( 2 ) INFORMATION FOR SEQ ID NO:2:

( i ) SEQUENCE CHARACTERISTICS:
        ( A ) LENGTH: 27 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

```
Asn  Pro  Val  Val  Leu  Glu  Leu  Ala  Ile  Leu  Asp  Leu  Asn  Ile  Val  Gln
1                   5                        10                       15
Ala  Gln  Phe  Gln  Glu  Glu  Leu  Lys  Glu  Ser  Phe
                    20                      25
```

( 2 ) INFORMATION FOR SEQ ID NO:3:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:

```
Gly  Lys  Val  Asn  Ala  Leu  Ile  Thr  Val  Ile  Asp  Asp  Ile  Tyr  Asp  Val
1                   5                        10                       15
Tyr  Gly  Thr  Leu
                    20
```

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

GARAARGANA CRGAYCARAT 20

( 2 ) INFORMATION FOR SEQ ID NO:5:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: cDNA ( i x ) FEATURE: N is inosine ( x i ) SEQUENCE DESCRIPTION: SEQ ID NO:5:

AAYATHGTNC ARGCNCARTT YCA 23

( 2 ) INFORMATION FOR SEQ ID NO:6:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:6:

AARGAYATHT AYGAYGT 17

( 2 ) INFORMATION FOR SEQ ID NO:7:

( i ) SEQUENCE CHARACTERISTICS:
( A ) LENGTH: 156 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:7:

GAGAGAGAAA GAGAGCGGAA GGAAAGATTA ATCATGGCTC TCAAAGTGTT AAGTGTTGCA 60

ACTCAAATGG CGATTCCTAG CAACCTAACG ACATGTCTTC AACCCTCACA CTTCAAATCT 120

TCTCCAAAAC TGTTATCTAG CACTAACAGT AGTAGT 156

( 2 ) INFORMATION FOR SEQ ID NO:8:

( i ) SEQUENCE CHARACTERISTICS:
( A ) LENGTH: 2182 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:8:

AGAGAGAGAG AGGAAGGAAA GATTAATCAT GGCTCTCAAA GTGTTAAGTG TTGCAACTCA 60

AATGGCGATT CCTAGCAACC TAACGACATG TCTTCAACCC TCACACTTCA AATCTTCTCC 120

AAAACTGTTA TCTAGCACTA ACAGTAGTAG TCGGTCTCGC CTCCGTGTGT ATTGCTCCTC 180

CTCGCAACTC ACTACTGAAA GACGATCCGG AAACTACAAC CCTTCTCGTT GGGATGTCAA 240

CTTCATCCAA TCGCTTCTCA GTGACTATAA GGAGGACAAA CACGTGATTA GGGCTTCTGA 300

GCTGGTCACT TTGGTGAAGA TGGAACTGGA GAAAGAAACG GATCAAATTC GACAACTTGA 360

| | | | | | |
|---|---|---|---|---|---|
|GTTGATCGAT|GACTTGCAGA|GGATGGGGCT|GTCCGATCAT|TTCCAAAATG|AGTTCAAAGA|420|
|AATCTTGTCC|TCTATATATC|TCGACCATCA|CTATTACAAG|AACCCTTTTC|CAAAAGAAGA|480|
|AAGGGATCTC|TACTCCACAT|CTCTTGCATT|TAGGCTCCTC|AGAGAACATG|GTTTTCAAGT|540|
|CGCACAAGAG|GTATTCGATA|GTTTCAAGAA|CGAGGAGGGT|GAGTTCAAAG|AAAGCCTTAG|600|
|CGACGACACC|AGAGGATTGT|TGCAACTGTA|TGAAGCTTCC|TTTCTGTTGA|CGGAAGGCGA|660|
|AACCACGCTC|GAGTCAGCGA|GGGAATTCGC|CACCAAATTT|TTGGAGGAAA|AAGTGAACGA|720|
|GGGTGGTGTT|GATGGCGACC|TTTTAACAAG|AATCGCATAT|TCTTTGGACA|TCCCTCTTCA|780|
|TTGGAGGATT|AAAAGGCCAA|ATGCACCTGT|GTGGATCGAA|TGGTATAGGA|AGAGGCCCGA|840|
|CATGAATCCA|GTAGTGTTGG|AGCTTGCCAT|ACTCGACTTA|AATATTGTTC|AAGCACAATT|900|
|TCAAGAAGAG|CTCAAAGAAT|CCTTCAGGTG|GTGGAGAAAT|ACTGGGTTTG|TTGAGAAGCT|960|
|GCCCTTCGCA|AGGGATAGAC|TGGTGGAATG|CTACTTTTGG|AATACTGGGA|TCATCGAGCC|1020|
|ACGTCAGCAT|GCAAGTGCAA|GGATAATGAT|GGGCAAAGTC|AACGCTCTGA|TTACGGTGAT|1080|
|CGATGATATT|TATGATGTCT|ATGGCACCTT|AGAAGAACTC|GAACAATTCA|CTGACCTCAT|1140|
|TCGAAGATGG|GATATAAACT|CAATCGACCA|ACTTCCCGAT|TACATGCAAC|TGTGCTTTCT|1200|
|TGCACTCAAC|AACTTCGTCG|ATGATACATC|GTACGATGTT|ATGAAGGAGA|AAGGCGTCAA|1260|
|CGTTATACCC|TACCTGCGGC|AATCGTGGGT|TGATTTGGCG|GATAAGTATA|TGGTAGAGGC|1320|
|ACGGTGGTTC|TACGGCGGGC|ACAAACCAAG|TTTGGAAGAG|TATTTGGAGA|ACTCATGGCA|1380|
|GTCGATAAGT|GGGCCCTGTA|TGTTAACGCA|CATATTCTTC|CGAGTAACAG|ATTCGTTCAC|1440|
|AAAGGAGACC|GTCGACAGTT|TGTACAAATA|CCACGATTTA|GTTCGTTGGT|CATCCTTCGT|1500|
|TCTGCGGCTT|GCTGATGATT|TGGGAACCTC|GGTGGAAGAG|GTGAGCAGAG|GGATGTGCC|1560|
|GAAATCACTT|CAGTGCTACA|TGAGTGACTA|CAATGCATCG|GAGGCGGAGG|CGCGGAAGCA|1620|
|CGTGAAATGG|CTGATAGCGG|AGGTGTGGAA|GAAGATGAAT|GCGGAGAGGG|TGTCGAAGGA|1680|
|TTCTCCATTC|GGCAAAGATT|TTATAGGATG|TGCAGTTGAT|TTAGGAAGGA|TGGCGCAGTT|1740|
|GATGTACCAT|AATGGAGATG|GGCACGGCAC|ACAACACCCT|ATTATACATC|AACAAATGAC|1800|
|CAGAACCTTA|TTCGAGCCCT|TTGCATGAGA|GATGATGACG|AGCCATCGTT|TACTTACTTA|1860|
|AATTCTACCA|AAGTTTTTCG|AAGGCATAGT|TCGTAATTTT|TCAAGCACCA|ATAAATAAGG|1920|
|AGAATCGGCT|CAAACAAACG|TGGCATTTGC|CACCACGTGA|GCACAAGGGA|GAGTCTGTCG|1980|
|TCGTTTATGG|ATGAACTATT|CAATTTTTAT|GCATGTAATA|ATTAAGTTCA|AGTTCAAGAG|2040|
|CCTTCTGCAT|ATTTAACTAT|GTATTGAAT|TTATCGAGTG|TGATTTCTG|TCTTTGGCAA|2100|
|CATATATTTT|TGTCATATGT|GGCATCTTAT|TATGATATCA|TACAGTGTTT|ATGGATGATA|2160|
|TGATACTATC|AAAAAAAAAA|AA| | | |2182|

( 2 ) INFORMATION FOR SEQ ID NO:9:

( i ) SEQUENCE CHARACTERISTICS:
        ( A ) LENGTH: 170 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

| | | | | | |
|---|---|---|---|---|---|
|ATTAATCCTA|GAAAACATA|GAAAGAGAGC|GGAAGGAAAG|ATTAATCATG|GCTCTCAAAG|60|
|TGTTAAGTGT|TGCAACTCAA|ATGGCGATTC|CTAGCAACCT|AACGACATGT|CTTCAACCCT|120|

CACACTTCAA ATCTTCTCCA AAACTGTTAT CTAGCACTAA CAGTAGTAGT                          170

( 2 ) INFORMATION FOR SEQ ID NO:10:

( i ) SEQUENCE CHARACTERISTICS:
    ( A ) LENGTH: 157 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:10:

TATCCAGCAC TAACAGTAGT AGTAGGTCTC GCCTCCGTGT GTATTTCTCC TCCTCGCAAC          60

TCACTACTGA AAGACGATCC GGAAACTACA ACCCTTCTCG TTGGATGTC AACTTCATCC          120

AATCGGTTCT CAGTGACTAT AAGGAGGACA AACACGT                                   157

( 2 ) INFORMATION FOR SEQ ID NO:11:

( i ) SEQUENCE CHARACTERISTICS:
    ( A ) LENGTH: 599 amino acids
    ( B ) TYPE: amino acid
    ( D ) TOPOLOGY: linear ( i i ) MOLECULE TYPE: protein ( x i ) SEQUENCE DESCRIPTION: SEQ ID NO:11:

```
Met Ala Leu Lys Val Leu Ser Val Ala Thr Gln Met Ala Ile Pro Ser
 1           5                   10                  15

Asn Leu Thr Thr Cys Leu Gln Pro Ser His Phe Lys Ser Ser Pro Lys
            20                  25                  30

Leu Leu Ser Ser Thr Asn Ser Ser Arg Ser Arg Leu Arg Val Tyr
        35                  40                  45

Cys Ser Ser Ser Gln Leu Thr Thr Glu Arg Arg Ser Gly Asn Tyr Asn
        50                  55                  60

Pro Ser Arg Trp Asp Val Asn Phe Ile Gln Ser Leu Leu Ser Asp Tyr
65                  70                  75                  80

Lys Glu Asp Lys His Val Ile Arg Ala Ser Glu Leu Val Thr Leu Val
                85                  90                  95

Lys Met Glu Leu Glu Lys Glu Thr Asp Gln Ile Arg Gln Leu Glu Leu
            100                 105                 110

Ile Asp Asp Leu Gln Arg Met Gly Leu Ser Asp His Phe Gln Asn Glu
        115                 120                 125

Phe Lys Glu Ile Leu Ser Ser Ile Tyr Leu Asp His His Tyr Tyr Lys
130                 135                 140

Asn Pro Phe Pro Lys Glu Glu Arg Asp Leu Tyr Ser Thr Ser Leu Ala
145                 150                 155                 160

Phe Arg Leu Leu Arg Glu His Gly Phe Gln Val Ala Gln Glu Val Phe
                165                 170                 175

Asp Ser Phe Lys Asn Glu Glu Gly Glu Phe Lys Glu Ser Leu Ser Asp
            180                 185                 190

Asp Thr Arg Gly Leu Leu Gln Leu Tyr Glu Ala Ser Phe Leu Leu Thr
        195                 200                 205

Glu Gly Glu Thr Thr Leu Glu Ser Ala Arg Glu Phe Ala Thr Lys Phe
    210                 215                 220

Leu Glu Glu Lys Val Asn Glu Gly Gly Val Asp Gly Asp Leu Leu Thr
225                 230                 235                 240

Arg Ile Ala Tyr Ser Leu Asp Ile Pro Leu His Trp Arg Ile Lys Arg
                245                 250                 255
```

```
Pro  Asn  Ala  Pro  Val  Trp  Ile  Glu  Trp  Tyr  Arg  Lys  Arg  Pro  Asp  Met
              260                      265                     270

Asn  Pro  Val  Val  Leu  Glu  Leu  Ala  Ile  Leu  Asp  Leu  Asn  Ile  Val  Gln
         275                      280                     285

Ala  Gln  Phe  Gln  Glu  Glu  Leu  Lys  Glu  Ser  Phe  Arg  Trp  Trp  Arg  Asn
     290                      295                     300

Thr  Gly  Phe  Val  Glu  Lys  Leu  Pro  Phe  Ala  Arg  Asp  Arg  Leu  Val  Glu
305                      310                     315                         320

Cys  Tyr  Phe  Trp  Asn  Thr  Gly  Ile  Ile  Glu  Pro  Arg  Gln  His  Ala  Ser
              325                      330                     335

Ala  Arg  Ile  Met  Met  Gly  Lys  Val  Asn  Ala  Leu  Ile  Thr  Val  Ile  Asp
              340                      345                     350

Asp  Ile  Tyr  Asp  Val  Tyr  Gly  Thr  Leu  Glu  Glu  Leu  Glu  Gln  Phe  Thr
              355                      360                     365

Asp  Leu  Ile  Arg  Arg  Trp  Asp  Ile  Asn  Ser  Ile  Asp  Gln  Leu  Pro  Asp
         370                      375                     380

Tyr  Met  Gln  Leu  Cys  Phe  Leu  Ala  Leu  Asn  Asn  Phe  Val  Asp  Asp  Thr
385                      390                     395                         400

Ser  Tyr  Asp  Val  Met  Lys  Glu  Lys  Gly  Val  Asn  Val  Ile  Pro  Tyr  Leu
              405                      410                     415

Arg  Gln  Ser  Trp  Val  Asp  Leu  Ala  Asp  Lys  Tyr  Met  Val  Glu  Ala  Arg
              420                      425                     430

Trp  Phe  Tyr  Gly  Gly  His  Lys  Pro  Ser  Leu  Glu  Glu  Tyr  Leu  Glu  Asn
              435                      440                     445

Ser  Trp  Gln  Ser  Ile  Ser  Gly  Pro  Cys  Met  Leu  Thr  His  Ile  Phe  Phe
     450                      455                     460

Arg  Val  Thr  Asp  Ser  Phe  Thr  Lys  Glu  Thr  Val  Asp  Ser  Leu  Tyr  Lys
465                      470                     475                         480

Tyr  His  Asp  Leu  Val  Arg  Trp  Ser  Ser  Phe  Val  Leu  Arg  Leu  Ala  Asp
              485                      490                     495

Asp  Leu  Gly  Thr  Ser  Val  Glu  Glu  Val  Ser  Arg  Gly  Asp  Val  Pro  Lys
              500                      505                     510

Ser  Leu  Gln  Cys  Tyr  Met  Ser  Asp  Tyr  Asn  Ala  Ser  Glu  Ala  Glu  Ala
          515                      520                     525

Arg  Lys  His  Val  Lys  Trp  Leu  Ile  Ala  Glu  Val  Trp  Lys  Lys  Met  Asn
     530                      535                     540

Ala  Glu  Arg  Val  Ser  Lys  Asp  Ser  Pro  Phe  Gly  Lys  Asp  Phe  Ile  Gly
545                      550                     555                         560

Cys  Ala  Val  Asp  Leu  Gly  Arg  Met  Ala  Gln  Leu  Met  Tyr  His  Asn  Gly
              565                      570                     575

Asp  Gly  His  Gly  Thr  Gln  His  Pro  Ile  Ile  His  Gln  Gln  Met  Thr  Arg
              580                      585                     590

Thr  Leu  Phe  Glu  Pro  Phe  Ala
          595
```

DNA ENCODING LIMONENE SYNTHASE FROM *MENTHA SPICATA*

This application is a continuation application of application Ser. No. 08/582,802, filed on Jan. 4, 1996, now abandoned, which was a continuation application of Ser. No. 08/145,941, filed on Oct. 28, 1993, now abandoned.

This invention was supported in part by grant number GM-31354 awarded by the National Institutes of Health. The government has certain rights in the invention.

FIELD OF THE INVENTION

The present invention relates to nucleic acid sequences which code for limonene synthase, a monoterpene cyclase enzyme, and to vectors containing the sequences, host cells containing the sequences and methods of producing recombinant limonene synthase.

BACKGROUND OF THE INVENTION

Several hundred naturally occurring, monoterpenes are known, and essentially all are biosynthesized from geranyl pyrophosphate, the ubiquitous $C_{10}$ intermediate of the isoprenoid pathway (Croteau and Cane, *Methods of Enzymology* 110:383–405 [1985]; Croteau, *Chem. Rev.* 87:929–954 [1987]). Monoterpene synthases, often referred to as "cyclases," catalyze the reactions by which geranyl pyrophosphate is cyclized to the various monoterpene carbon skeletons. These enzymes have received considerable recent attention because the cyclization process determines the basic character of the monoterpene end-products and because the cyclization mechanism is quite complex, involving multiple steps in which many of the carbon atoms of the substrate undergo alterations in bonding, hybridization, and configuration (Croteau and Cane, *Methods of Enzymology* 110:383–405 [1985]; Croteau, *Chem. Rev.* 87:929–954 [1987]). Research on monoterpene cyclases has also been stimulated by the possible regulatory importance of these enzymes that function at a branch point in isoprenoid metabolism (Gershenzon and Croteau, *Biochemistry of the Mevalonic Acid Pathway to Terpenoids* (Towers and Stafford, eds.), Plenum Press, New York, N.Y., pp. 99–160 [1990]) as well as by the commercial significance of the essential oils (Guenther, *The Essential Oils*, Vols. III–VI (reprinted) R. E. Krieger, Huntington, N.Y. [1972]) and aromatic resins (Zinkel and Russell, *Naval Stores: Production, Chemistry, Utilization*, Pulp Chemicals Association, New York [1989]) and the ecological roles of these terpenoid secretions, especially in plant defense (Gershenzon and Croteau, in "Herbivores: Their Interactions with Secondary Plant Metabolites," Vol. I, 2nd Ed. (Rosenthal and Berenbaum, eds.) Academic Press, San Diego, Calif., pp. 165–219 [1991]; Harbome, in "Ecological Chemistry and Biochemistry of Plant Terpenoids," (Harborne and Tomas-Barberan, eds.) Clarendon Press, Oxford, Mass., pp. 399–426 [1991]).

One of the major classes of plant monoterpenes is the monocyclic p-menthane (1-methyl-4-isopropylcyclohexane) type, found in abundance in members of the mint (Mentha) family. The biosynthesis of p-menthane monoterpenes in Mentha species, including the characteristic components of the essential oil of peppermint (i.e., (−)-menthol) and the essential oil of spearmint (i.e., (−)-carvone), proceeds from geranyl pyrophosphate via the cyclic olefin (−)-limonene (Croteau, *Planta Med.* 57 (suppl): 10–14 [1991]), as shown in FIG. 1. The transformation of geranyl pyrophosphate to limonene is seemingly the least complicated terpenoid cyclization (Croteau and Satterwhite, *J. Biol. Chem.* 264:15309–15315 [1989]) in having ample precedent in solvolytic model studies (Cramer and Rittersdorf, *Tetrahedron* 23:3015–3022 [1967]; Haley et al., *J. Chem. Soc. C.,* pp. 264–268 [1969]; Kobayashi et al., *Chem. Lett., pp.* 1137–1138 [1976]; Vial et al., *Tetrahedron* 37:2351–2357 [1981]), and the responsible enzyme has become a prototype for the terpenoid cyclization reaction (Cori, *Phytochemistry* 22:331–341 [1983]; Pauly et al., *Plant Cell Rep.* 5:19–22 [1984]; Suga et al., *Chem. Lett.*, pp. 115–118 [1988]; Pérez et al., *Plant Physiol. Biochem.* 28:221–229 [1990]; Rajaonarivony et al., *Arch. Biochem. Biophys.* 299:77–82 [1992]). The enzyme that produces the (−)-4S-enantiomer (geranyl pyrophosphate:(−)-4S-limonene cyclase or, simply, (−)-4S-limonene synthase) has been purified from peppermint (*Mentha x piperita*) and spearmint (*Mentha spicata*) oil glands (Alonso et al., *J. Biol. Chem.* 267:7582–7587 [1992]), and highly specific antibodies directed against this enzyme have been prepared (Alonso et al., *Arch. Biochem. Biophys.* 301:58–63 [1993]). In properties and mechanism of action (Rajaonarivony et al., *Arch. Biochem. Biophys.* 299:77–82 [1992]; Rajaonarivony et al., *Arch. Biochem. Biophys.* 296:49–57 [1992]), it seemingly catalyzes a slow, possibly rate-limiting, step of monoterpene biosynthesis in Mentha (Gershenzon and Croteau, *Biochemistry of the Mevalonic Acid Pathway to Terpenoids* (Towers and Stafford, eds.), Plenum Press, New York, N.Y., pp. 99–160 [1990]).

A detailed understanding of the control of monoterpene biosynthesis and of the cyclase reaction mechanism requires the relevant cDNA clones as tools for evaluating patterns of developmental and environmental regulation and for examining active site structure function relationships. There have been no previous reports of the cloning of a monoterpene cyclase although the molecular cloning of a sesquiterpene cyclase of plant origin (epi-aristolochene synthase from tobacco) has recently been reported (Facchini and Chappell, *Proc. Natl. Acad. Sci. USA* 89:11088–11092 [1992]), and the cloning of a diterpene cyclase (casbene synthase from castor bean) has also been accomplished.

SUMMARY OF THE INVENTION

In accordance with the foregoing, cDNA encoding (−)-4S-limonene synthase from spearmint has been isolated and sequenced, and the corresponding amino acid sequence has been determined. Accordingly, the present invention relates to isolated DNA sequences which code for the expression of limonene synthase, such as the sequence designated SEQ ID No:11 which encodes limonene synthase from spearmint (*Mentha spicata*). In other aspects, the present invention is directed to replicable recombinant cloning vehicles comprising a nucleic acid sequence, e.g., a DNA sequence, which codes for limonene synthase or for a base sequence sufficiently complementary to at least a portion of the limonene synthase DNA or RNA to enable hybridization therewith (e.g., antisense limonene synthase RNA or fragments of complementary limonene synthase DNA which are useful as polymerase chain reaction primers or as probes for limonene synthase or related genes). In yet other aspects of the invention, modified host cells are provided that have been transformed, transfected, infected and/or injected with a recombinant cloning vehicle and/or DNA sequence of the invention. Thus, the present invention provides for the recombinant expression of limonene synthase, and the inventive concepts may be used to facilitate the production, isolation and purification of significant quantities of recombinant limonene synthase (or of the primary enzyme product, limonene) for subsequent use, to obtain expression or enhanced expression of limonene synthase in plants to attain enhanced limonene production as a predator defense mechanism, or may be otherwise employed in an environment where the regulation or expression of limonene synthase is desired for the production of limonene synthase or the enzyme product, limonene.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIGS. 2A to 2C show the amino acid sequences of peptides derived by CNBr cleavage and V8 proteolysis of limonene synthase as described in Example 4. Also shown are oligonucleotide probes derived from the peptide sequences, as well as degenerate nucleotide substitutions in the oligomers. FIG. 2A shows the peptide fragment designated CNBr #1 (99–119) (SEQ ID No:1) together with a corresponding 20-mer probe (SEQ ID No:4) and degenerate probe codings. FIG. 2B shows the peptide fragment designated CNBr #2 (273–299) (SEQ ID No:2) together with a corresponding 23-mer probe (SEQ ID No:5) and degenerate probe codings. The solid line over CNBr #2 indicates the overlapping fragment V8 #1. FIG. 2C shows the peptide designated CNBr #3 (342–361) (SEQ ID No:3) together with a 17-mer probe (SEQ ID No:6) and degenerate probe codings;

FIGS. 4A to 4C show the nucleotide (SEQ ID No:8) and predicted amino acid sequence (SEQ ID No:11) of spearmint limonene cyclase clone pLC 5.2, and a comparison of the 5'-nucleotide sequence of spearmint limonene cyclase clone pLC 5.2 with partial sequences from pLC 4.1 (SEQ ID No:7), pLC 8.5 (SEQ ID No:9) and pLC 10.1 (SEQ ID No:10). As shown in FIG. 4, the start and stop codons and the Shine-Delgarno sequences are underlined (_). The sequences of CNBr fragments #1, 2 and 3 (SEQ ID No:1, SEQ ID No:2 and SEQ ID No:3, respectively) are double underlined (_). Differences in the nucleotide sequences between pLC 4.1, 8.5 and 10.1, as compared to pLC 5.2, are indicated by lower case letters;

FIGS. 6A and 6B show an amino acid comparison of spearmint limonene cyclase (bolded lines, SEQ ID No:11) with tobacco epi-aristolochene synthase (bottom) and castor bean casbene synthase (top), with amino acid residues 1 through 391 of spearmint limonene cyclase being shown in FIG. 6A and amino acid residues 392 through 599 of spearmint limonene cyclase being shown in FIG. 6B. The vertical bars (|) in FIG. 6 mark identical residues. One dot (.) and two dots (:) indicate that two and one point mutations, respectively, are required to produce a match with spearmint limonene cyclase. Asterisks are marked above conserved histidine and cysteine residues in the three proteins. Putative metal ion-substrate complex binding domains are underlined (_).

DETAILED DESCRIPTION OF THE PREFERRED EMBODIMENT

Figure 1:
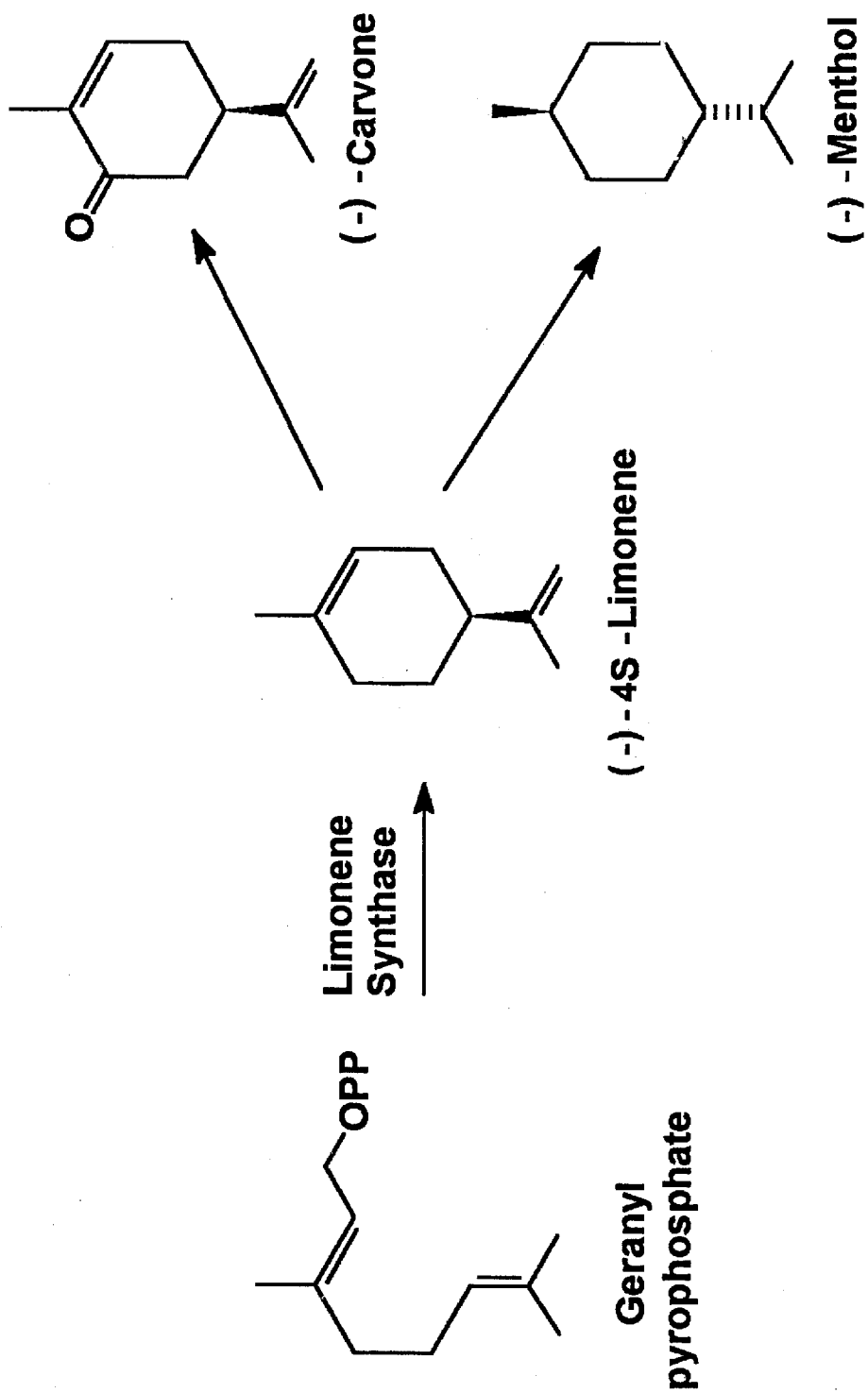
FIG. 1 is a schematic representation of the principal pathways of monoterpene biosynthesis in spearmint leading to carvone and in peppermint leading to menthol. After geranyl pyrophosphate is cyclized to limonene, a series of secondary redox transformations convert this olefinic intermediate to other monoterpenes.

As used herein, the terms "amino acid" and "amino acids" refer to all naturally occurring L-α-amino acids or their residues. The amino acids are identified by either the single-letter or three-letter designations:

| Asp | D | aspartic acid | Ile | I | isoleucine |
|-----|---|---------------|-----|---|------------|
| Thr | T | threonine | Leu | L | leucine |
| Ser | S | serine | Tyr | Y | tyrosine |
| Glu | E | glutamic acid | Phe | F | phenylalanine |
| Pro | P | proline | His | H | histidine |
| Gly | G | glycine | Lys | K | lysine |
| Ala | A | alanine | Arg | R | arginine |
| Cys | C | cysteine | Trp | W | tryptophan |
| Val | V | valine | Gln | Q | glutamine |
| Met | M | methionine | Asn | N | asparagine |

The terms "limonene synthase" and "limonene cyclase" are used synonymously herein to mean the enzyme, particularly from *Mentha spicata*, capable of catalyzing the cyclization of geranyl phosphate to (−)-4S-limonene, as described herein.

The terms "alteration", "amino acid sequence alteration", "variant" and "amino acid sequence variant" refer to limonene synthase molecules with some differences in their amino acid sequences as compared to native limonene synthase. Ordinarily, the variants will possess at least 80% homology with native limonene synthase, and preferably, they will be at least about 90% homologous with native limonene synthase. The amino acid sequence variants of limonene synthase falling within this invention possess substitutions, deletions, and/or insertions at certain positions. Sequence variants of limonene synthase may be used to attain desired enhanced or reduced enzymatic activity, altered product distribution such as enhanced production of the normally minor co-products α-pinene, β-pinene and/or myrcine, and the like.

Substitutional limonene synthase variants are those that have at least one amino acid residue in the native limonene synthase sequence removed and a different amino acid inserted in its place at the same position. The substitutions may be single, where only one amino acid in the molecule has been substituted, or they may be multiple, where two or more amino acids have been substituted in the same molecule. Substantial changes in the activity of the limonene synthase molecule may be obtained by substituting an amino acid with a side chain that is significantly different in charge and/or structure from that of the native amino acid. This type of substitution would be expected to affect the structure of the polypeptide backbone and/or the charge or hydrophobicity of the molecule in the area of the substitution.

Moderate changes in the activity of the limonene synthase molecule would be expected by substituting an amino acid with a side chain that is similar in charge and/or structure to that of the native molecule. This type of substitution, referred to as a conservative substitution, would not be expected to substantially alter either the structure of the polypeptide backbone or the charge or hydrophobicity of the molecule in the area of the substitution.

Insertional limonene synthase variants are those with one or more amino acids inserted immediately adjacent to an amino acid at a particular position in the native limonene synthase molecule. Immediately adjacent to an amino acid means connected to either the α-carboxy or α-amino functional group of the amino acid. The insertion may be one or more amino acids. Ordinarily, the insertion will consist of one or two conservative amino acids. Amino acids similar in charge and/or structure to the amino acids adjacent to the site of insertion are defined as conservative. Alternatively, this invention includes insertion of an amino acid with a charge and/or structure that is substantially different from the amino acids adjacent to the site of insertion.

Deletional variants are those with one or more amino acids in the native limonene synthase molecule removed. Ordinarily, deletional variants will have one or two amino acids deleted in a particular region of the limonene synthase molecule.

The terms "biological activity", "biologically active", "activity" and "active" refer to the ability of the limonene synthase molecule to convert geranyl pyrophosphate to (−)-4S-limonene and co-products as measured in an enzyme activity assay, such as the assay described in Example 3 below. Amino acid sequence variants of limonene synthase may have desirable altered biological activity including, for example, altered reaction kinetics, product distribution or other characteristics.

The terms "DNA sequence encoding", "DNA encoding" and "nucleic acid encoding" refer to the order or sequence of deoxyribonucleotides along a strand of deoxyribonucleic acid. The order of these deoxyribonucleotides determines the order of amino acids along the polypeptide chain. The DNA sequence thus codes for the amino acid sequence.

The terms "replicable expression vector" and "expression vector" refer to a piece of DNA, usually double-stranded, which may have inserted into it a piece of foreign DNA. Foreign DNA is defined as heterologous DNA, which is DNA not naturally found in the host cell. The vector is used to transport the foreign or heterologous DNA into a suitable host cell. Once in the host cell, the vector can replicate independently of the host chromosomal DNA, and several copies of the vector and its inserted (foreign) DNA may be generated. In addition, the vector contains the necessary elements that permit translating the foreign DNA into a polypeptide. Many molecules of the polypeptide encoded by the foreign DNA can thus be rapidly synthesized.

The terms "transformed host cell" and "transformed" refer to the introduction of DNA into a cell. The cell is termed a "host cell", and it may be a prokaryotic or a eukaryotic cell. Typical prokaryotic host cells include various strains of E. coli. Typical eukaryotic host cells are plant cells, such as maize cells. The introduced DNA is usually in the form of a vector containing an inserted piece of DNA. The introduced DNA sequence may be from the same species as the host cell or a different species from the host cell, or it may be a hybrid DNA sequence, containing some foreign and some homologous DNA.

In accordance with the present invention, cDNA encoding limonene synthase was isolated and sequenced in the following manner. -(−)-4S-Limonene synthase is located exclusively in the glandular trichome secretory cells and catalyzes the first step of monoterpene biosynthesis in these essential oil species. Known methods for selectively isolating secretory cell clusters from these epidermal oil glands (Gershenzon et al., *Modern Phytochemical Methods* (Fischer et al., Eds.), Plenum Press, New York, N.Y., pp. 347–370 [1991]; Gershenzon et al., *Anal. Biochem.* 200:130–138 [1992]) and for purifying this monomeric cyclase ($M_r$~56,000) from these structures (Alonso and Croteau, *Methods Plant Biochem.* 9:239–260 [1993]; Lanznaster and Croteau, *Protein Express. Purif.* 2:69–74 [1991]) were employed to obtain sufficient amounts of protein from spearmint for polyclonal antibody production (Alonso et al., *Arch. Biochem. Biophys.*, supra) and amino acid sequence analysis. Since the amino terminus of the cyclase was blocked, internal fragments were generated by CNBr cleavage and V8 proteolysis. Several of these fragments, comprising approximately 15% of the protein, were successfully sequenced and subsequently shown to span about half of the length of the protein starting from near the amino terminus (FIG. 2). From this information three non-overlapping, degenerate oligonucleotide probes (20-mer, 23-mer and 17-mer) were identified having the degenerate codings:

| | |
|---|---|
| 20-mer GARAARGANACRGAYCARAT | (SEQ ID No:4) |
| 23-mer AAYATHGTNCARGCNCARTTYCA | (SEQ ID No:5) |
| 17-mer AARGAYATHTAHGAYGT | (SEQ ID No:6) |

As used herein, nucleotides are represented by the symbols recommended by the IUPAC-IUB Biochemical Nomenclature Commission, wherein A is adenine, C is cytosine, G is guanine, T is thymine, R is A or G, N is A or G or T or C or other, Y is C or T and H is A or C or T. Corresponding probes were prepared and used to screen a λZAP cDNA expression library, as described in Example 5, infra. The probes employed were as follows:

20-mer GAAAAAGAAACAGATCAGAT (SEQ ID No:4)
where 3R=A, 6R=A, 9N=A, 12R=A, 15Y=T and 18R=G)

23-mer AATATTGTTCAAGCICAATTTCA (SEQ ID No:5)
where 3Y=T, 6H=T, 9N=inosine, 12R=A, 15N=inosine, 18R=A and 21Y=T)

17-mer AAGGATATTTACGATGT (SEQ ID No:6)
where 3R=G, 6Y=T, 9H=T, 12Y=C and 15Y=T)

Four clones, designated pLC 4.1, pLC 5.2, pLC 8.5 and pLC 10.1, hybridized to all three oligonucleotides and persisted through four subsequent rounds of screening and purification. The isolated phagemids were in vivo excised, circularized, and packaged; these phagemids (plasmids) were then used to transfect *E. coli* XL1-Blue (Skratagene) in accordance with the manufacturer's instructions as described, infra. The transfected cultures were induced with IPTG, and the cells from each were harvested, homogenized and assayed for limonene cyclase activity using $[1-^3H]$ geranyl pyrophosphate as substrate. Preparations from three of the four transfected cultures (with pLC 4.1, 5.2 and 8.5) afforded levels of limonene synthase activity in the range of 10–50 nmol/culture with specific activities in the range of 0.5–1.0 nmol/h/mg protein. The plasmid pLC 5.2 has been deposited on Oct. 26, 1993 in the American Type Culture Collection, Rockville, Md., USA, under accession number ATCC 75581.

Figure 3:
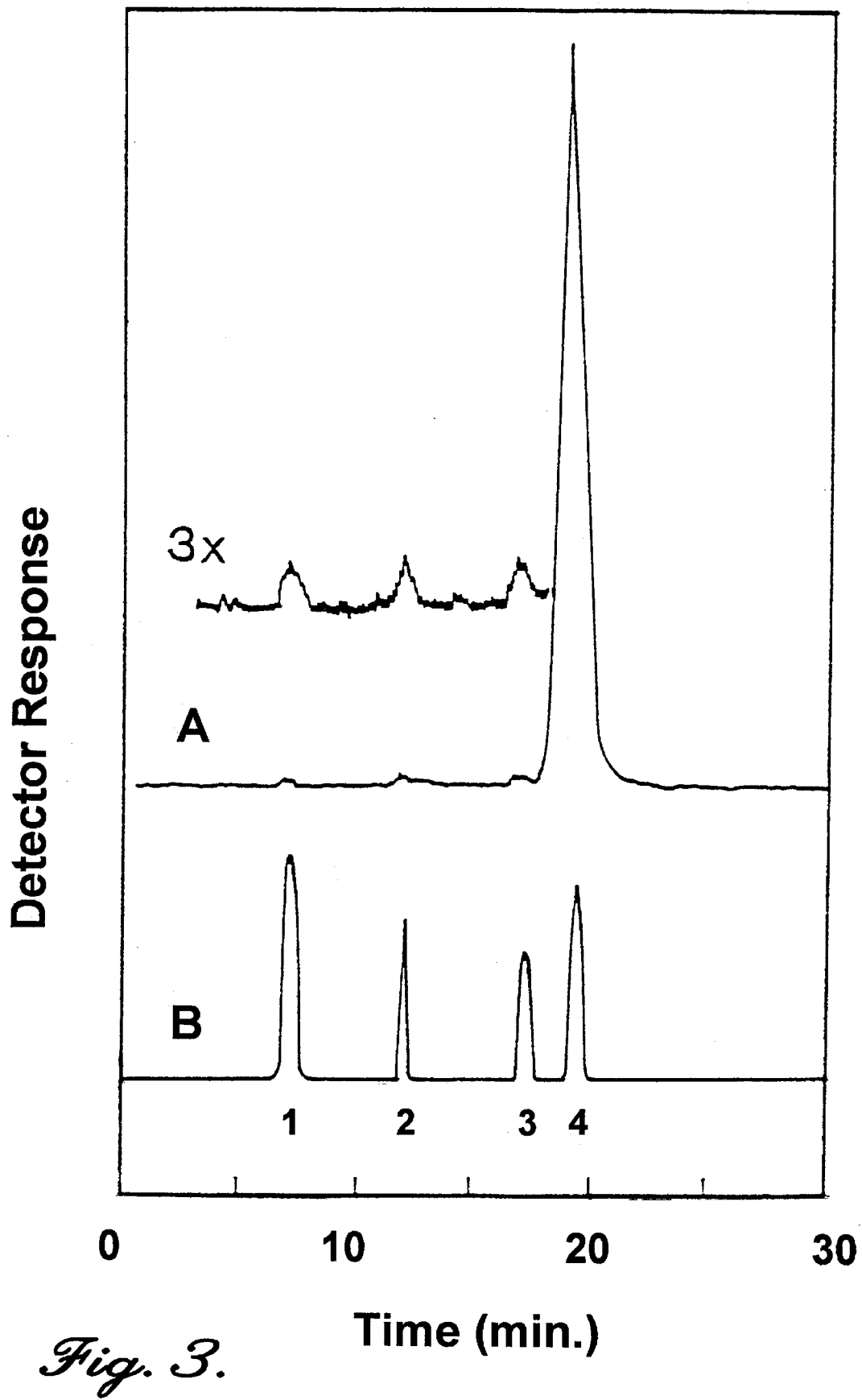
FIG. 3 is a graphical representation of thermal conductivity detector response in the radio-GLC separation of limonene from other monoterpene olefins generated by recombinant limonene synthase, as described in Example 7. Tracing B represents the detector response to authentic standards of α-pinene (1), β-pinene (2), myrcene (3) and limonene (4). Tracing A represents the detector response to the actual products resulting from expression of (4S)-limonene synthase. Tracing 3X represents a 3X amplified response for the minor components (1), (2) and (3) of tracing A.

To examine in greater detail the product mixture generated by the recombinant limonene cyclases, the proteins encoded by pLC 4.1, 5.2 and 8.5 were partially purified by anion-exchange chromatography on DEAE-Sepharose. A single olefin synthase per clone was observed on fractionation, and preparative-scale incubations with each were carried out in the presence of saturating concentrations of divalent metal ion cofactor ($Mg^{2+}$) and [1-$^3$H]geranyl pyrophosphate. The pentane-soluble reaction products were isolated and passed through silica gel to provide the olefin fraction. Following the addition of authentic monoterpene carriers, this material was analyzed by radio-GLC as described in Example 8 and shown to contain primarily limonene (~94%) with smaller amounts of other olefins (FIG. 3). Integration of the amplified signal gave 1.8% α-pinene, 2.0% β-pinene and 1.9% myrcene, which is identical to the levels of these minor coproducts generated by the limonene synthase from spearmint and peppermint (Rajaonarivony et al., *Arch. Biochem. Biophys.*, supra). Thus, the recombinant proteins produced by pLC 4.5, 5.2 and 8.5 generated, with complete fidelity, the same product mixture as the native enzyme. The production of multiple products, while seemingly common among monoterpene synthases (Croteau, *Chem. Rev.*, supra; Alonso and Croteau, in *Secondary Metabolite Biosynthesis and Metabolism* (Petroski and McCormick, Eds.), Plenum Press, New York, N.Y., pp. 239–251 [1992]), is an unusual enzymatic phenomenon that can be verified by isotopically sensitive branching experiments (Alonso and Croteau, in *Secondary Metabolite Biosynthesis and Metabolism*, supra; Wagschal et al., *Tetrahedron* 47:5933–5944 [1991]) but not, with certainty, by either co-purification or differential inactivation studies (Rajaonarivony et al., *Arch. Biochem. Biophys*, supra; Alonso et al., *J. Biol. Chem.*, supra). The production of multiple products by a recombinant cyclase provides the ultimate proof of this unusual catalytic capability.

Since the pLC 5.2 cDNA gave the highest apparent specific activity of limonene cyclase expression, this isolate was completely sequenced and examined in detail (FIG. 4). The pLC 5.2 limonene synthase cDNA (SEQ ID No:8) is 2182 nucleotides in length and contains a complete open reading frame of 1800 nucleotides. The deduced amino acid sequence indicates the presence of a putative plastidial transit peptide of approximately 89 amino acids (SEQ ID No:11, residues 1–89) and a mature protein of approximately 510 residues (SEQ ID No:11, residues 90–599). The locations of all four peptide sequence fragments obtained from the native protein have been identified within the open reading frame of pLC 5.2 (FIG. 4), confirming the cDNA to represent a limonene synthase gene.

The transit peptide/mature protein junction and, thus, the exact lengths of both moieties are unknown because the amino terminus of the mature protein is blocked and has not yet been identified. The approximate size and charge of the leader sequence is appropriate for a plastidial transit peptide; the first 89 amino acids are characteristically high in serine and threonine content (~25%); and the Chou-Fasman rules (Chou and Fasman, *Adv. Enzymol.* 47:45–147 [1978]) indicate a typical β-sheet adjacent to the putative cleavage site (Keegstra et al., *Ann. Rev. Plant Physiol. Plant Mol. Biol.* 40:471–501 [1989]; von Heijne et al., *Eur. J. Biochem.* 180:535–545 [1989]; von Heijne and Nishikawa, *FEBS Lett.* 278:1–3 [1991]) which established criteria (von Heijne, *Eur. J. Biochem.* 133:17–21 [1983]) predict between or near residues Ala 89-Ser 90. The location of the CNBr fragment #1 along the deduced amino acid sequence defines the minimum size of the mature peptide since no fragments preceding Met 98 were observed. Translation of the putative mature limonene synthase cDNA (i.e., SEQ ID No:11, residues 90–599) yields a protein of 59.8 kD, which is within 10% of the 56 kD mass of the native (mature) enzyme estimated by gel permeation chromatography and SDS-PAGE (Alonso et al., *J. Biol. Chem.*, supra). Additionally, the deduced amino acid composition of the translated pLC 5.2 cDNA open reading frame corresponding to the putative mature peptide (amino acid residues 90–599) agrees very well with the amino acid composition of the native enzyme, as shown in Table 1:

TABLE 1

Amino acid composition of native limonene cyclase compared to that of the translated cDNA

| Amino Acid | Deduced from translated cDNA | Acid hydrolyzed native protein |
|---|---|---|
| Ala | 25 | 29 |
| Cys | 5 | ND |
| Asp + Asn | 56 | 63 |
| Glu + Gln | 68 | 74 |
| Phe | 28 | 23 |
| Gly | 24 | 36 |
| His | 14 | 12 |
| Ile | 26 | 24 |
| Lys | 27 | 27 |
| Leu | 55 | 58 |
| Met | 14 | ND |
| Pro | 17 | 15 |
| Arg | 30 | 26 |
| Ser | 32 | 28 |
| Thr | 23 | 22 |
| Val | 32 | 31 |
| Trp | 13 | ND |
| Tyr | 21 | 17 |
| Total residues | 510 | |
| kD | 59.8 | |

The translated sequence includes only those amino acids of the putative mature peptide, residues #90–599. Asn/Asp and Gln/Glu could not be distinguished, and tryptophan, methionine and cysteine could not be determined (ND) from the acid hydrolyzed sample. The molecular weight of the native protein was determined by SDS-PAGE and gel permeation chromatography to be about 56,000. The $\chi^2$ test showed interdependence of the two compositions with p>0.97.

Finally, ultrastructural immunogold cytochemical studies with anti-limonene cyclase polyclonal antibodies have recently demonstrated the limonene cyclase of mint to be located exclusively in the plastids (leucoplasts) of the glandular trichomes, a finding entirely consistent with the presence of such an organellar targeting sequence in the limonene synthase cDNA. Although the limonene synthase cDNA set forth in SEQ ID No:8 directs the enzyme to plastids, substitution of the targeting sequence (SEQ ID No:11, residues 1 to 89) with other transport sequences well known in the art (see, e.g., Keegstra et al., supra; von Heijne et al., supra) may be employed to direct the limonene synthase to other cellular or extracellular locations.

Spearmint (*M. spicata*) is a tetraploid and parent of peppermint (*M. piperita=Mentha aquatica x spicata*), a hexaploid (Harley and Brighton, *Bot. J. Linn. Soc.* 74:71–96 [1977]). Both contain ostensibly the same limonene synthase (Alonso et al., *J. Biol. Chem.*, supra). RNA blot hybridization of pLC 5.2 insert DNA to spearmint and peppermint poly(A)$^+$ RNA verified the presence of the homologous sequences in both species and provided an estimate of limonene cyclase mRNA transcript size of about 2,400 nucleotides (data not shown). Thus, all lines of evidence, including RNA blot hybridization, indicate that the limonene synthase structural gene from spearmint has been successfully isolated. All peptide sequence fragments obtained from the native enzyme correspond to sequences identified in the pLC 5.2 open reading frame, which is of the correct size and amino acid composition (excluding the putative transit peptide). The recombinant enzyme when expressed in *E. coli* is immunologically recognized by polyclonal antibodies raised to the purified limonene synthase from spearmint and is catalytically active in generating a product distribution identical to that of the native cyclase.

The other full-length clones were partially sequenced and, although the first 100 nucleotides downstream of the translation start were identical in the cDNA inserts of pLC 4.1, pLC 5.2 and pLC 8.5, suggesting that they share a common open reading frame, several nucleotide differences were observed in the 5'-untranslated regions of all three (FIG. 4). These differences suggest the presence of several limonene synthase genes and/or alleles in the allotetraploid spearmint genome, which has been confirmed by DNA blot (Southern blot) hybridization. A sesquiterpene cyclase, epi-aristolochene synthase, from tobacco is encoded by a gene family (Facchini and Chappell, *Proc. Natl. Acad. Sci. USA*, supra). Partial sequencing of the clone pLC 10.1, that was inactive in limonene synthase expression, revealed a truncated transit peptide and several point mutations in the coding region (FIG. 4). Additionally, the open reading frame of pLC 10.1 was out of frame with the lacZ translation initiation site. However, this complication alone is insufficient to explain the lack of expression since all of the other (full-length) cDNAs were also out of frame but nevertheless afforded functional expression of the limonene synthase.

Figure 5:
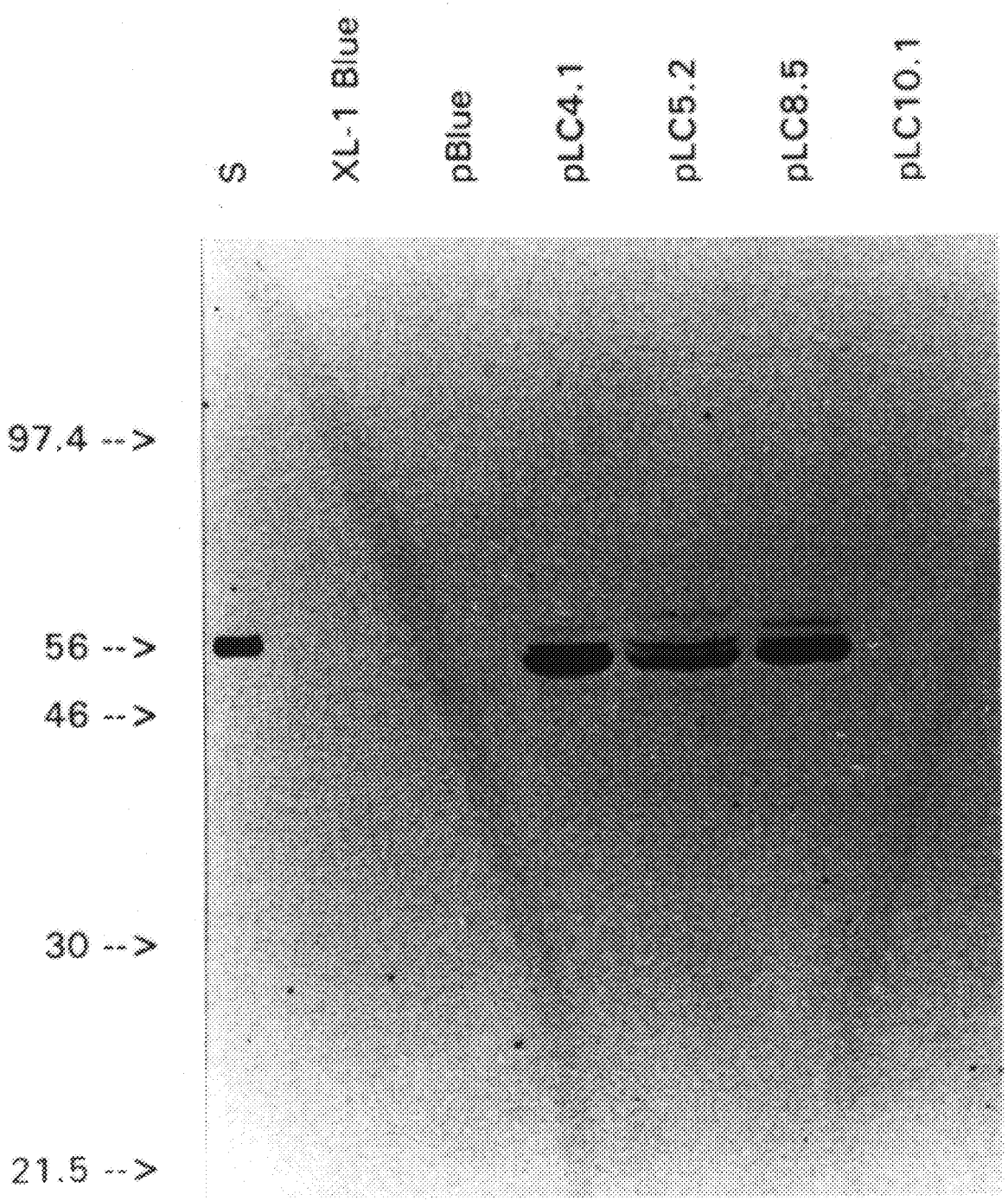
FIG. 5 is an immunoblot of crude protein extracts which were subjected to SDS-PAGE and then probed with anti-limonene synthase polyclonal antibodies, as described in Example 7. The immunoblot lanes are: native limonene synthase from spearmint (S); preparations from *E. coli* alone (XL-1 Blue) and *E. coli* transformed with Bluescript containing no insert (pBlue); and the clones pLC 4.1, pLC 5.2, pLC 8.5 and pLC 10.1, respectively. The migration of protein standards (in kDa) is also indicated.

Based on the length of the full open reading frame, including the putative transit peptide, the transfected cultures should express a protein of at least 69 kD; however, immunoblot analysis of total cell extracts from all of the functional cultures as described in Example 8 exhibited no detectable antigen of this molecular weight but rather a single major peptide at 54 kD (compared to native enzyme at 56 kD) (FIG. 5). The most plausible explanation for the origin of this immunopositive 54 kD peptide (and the larger peptides of lower abundance) is that translation reinitiation or run-through translation occurs. Proteolytic processing of the immature peptide by *E. coli* enzymes may also take place, much the same way as in spearmint plastids. Several leader peptidases of *E. coli* are similar to higher plant plastidal transit peptidase (Gottesman et al., *Proc. Natl. Acad. Sci. USA* 87:3513–3517 [1990]; Halpin et al., *EMBO J.* 8:3917–3922 [1989]) and such processing of a recombinant plastid-directed enzyme has been described previously (Meadows and Robinson, *Plant Mol. Biol.* 17:1241–1243 [1991]). As observed in preliminary immunoblots, *E. coli* bearing Bluescript II SK(+) alone or cDNA pLC 10.1 did not express recognizable cyclase antigen using the purified antibody preparation (FIG. 5). This evidence indicates that although the cDNA is capable of being translated into proteins up to 69 kD, peptides as short as 59 kD are still biologically active as limonene synthase.

Homology with other terpene cyclases—Searches of GenPept, PIR and SwissProt databases (Altschul et al., *J. Mol. Biol.* 215:403–410 [1990]) revealed no sequences with significant similarity to limonene synthase, nor did the sequence of limonene synthase resemble those of any of the microbial sesquiterpene cyclases that have been recently determined, including the Fusarium and Gibberella trichodiene synthases (Hohn and Beremand, *Gene* 79:131–138 [1989]; Hohn and Desjardins, *Mol. Plant-Microbe Interact.* 5:249–256 [1992]), the Penicillium artistolochene synthase (Proctor and Hohn, *J. Biol. Chem.* 268:4543–4548 [1993]) and the streptomyces pentalenene synthase. However, sequence comparison (Devereaux et al., *Nucleic Acids Res.* 12:387–395 [1984]) to other terpene cyclases from higher plants revealed a significant degree of sequence similarity. The limonene synthase from spearmint showed 34% identity and 56% similarity (based on conservative amino acid substitutions) to a sesquiterpene cyclase, epi-aristolochene synthase, from tobacco (Facchini and Chappell, *Proc. Natl. Acad. Sci. USA*, supra), and 31% identity and 53% similarity to a diterpene cyclase, casbene synthase, from castor bean (as shown in FIG. 6). These plant terpenoid synthases represent three different types of cyclases from three diverse families, a monoterpene cyclase from the Lamiaceae, a sesquiterpene cyclase from the Solanaceae and a diterpene cyclase from the Euphorbiaceae suggesting a common ancestry for this class of enzymes.

Recent evidence has implicated histidine and cysteine residues at the active site of limonene synthase and of several other monoterpene and sesquiterpene cyclases (Rajaonarivony et al., *Arch. Biochem. Biophys.*, supra). A search of the aligned sequences of limonene synthase, epi-aristolochene synthase, and casbene synthase revealed the presence of four such conserved residues, positioned at amino acids 124, 167, 251 and 516 of limonene cyclase (SEQ ID No:11; represented by * locations in FIG. 6).

The limonene synthase sequence does not resemble any of the published sequences for prenyltransferases (Clarke et al., *Mol. Cell. Biol.* 7:3138–3146 [1987]; Anderson et al., *J. Biol. Chem.* 264:19176–19184 [1989]; Ashby and Edwards, *J. Biol. Chem.* 265:13157–13164 [1990]; Carattoli et al., *J. Biol. Chem.* 266:5854–5859 [1991]; Fujisaki et al., *J. Biochem.* 108:995–1000 [1990]), a group of enzymes that, like the terpenoid cyclases, employ allylic pyrophosphate substrates and exploit similar electrophilic reaction mechanisms (Poulter and Rilling, supra). The sequence (I,L,V) XDDXXD occurs in two of the three homologous domains of several prenyltransferases of diverse origin (Math et al., *Proc. Natl. Acad. Sci. USA* 89:6761–6764 [1992]), and it has been suggested that these aspartate-rich elements function in binding the divalent metal ion complexed pyrophosphate moiety of the prenyl substrates (Ashby et al., in *Molecular Biology of Atherosclerosis* (Attie, Ed.), Elsevier, Amsterdam, pp. 27–34 [1990]). The terpenoid cyclases would be expected to exhibit similar substrate binding requirements, and most (Facchini and Chappell, supra; Hohn and Beremand, supra; Hohn and Desjardins, supra), but not all (Proctor and Hohn, supra), sesquiterpene cyclase sequences contain this motif. The deduced limonene cyclase peptide sequence contains the element VIDDIYD at SEQ ID No:11 residues 350–356 and the related sequence VDDTSYD at SEQ ID No:11 residues 397–403. The former motif is strongly conserved in the three plant-derived cyclase genes, but the latter is not, and neither is near the four conserved histidine and cysteine residues. Cane (*Genetics and Biochemistry of Antibiotic Production* (Vining and Stuttard, Eds.), Butterworth-Heinemann, Stoneham, Mass., in press [1993]) has urged caution in interpreting the functional role of these aspartate-rich motifs and has pointed out an additional motif in prenyltransferases and cyclases that is rich in basic amino acids and that has been implicated at the active site of farnesyl pyrophosphate synthase (Brems et al., *Biochemistry* 20:3711–3718 [1981]). Similar patches of charged amino acids have been described in other terpenoid synthases (Chamovitz et al., *FEBS Lett.* 296:305–311 [1992]), but neither region has very close analogy in the limonene synthase sequence.

The isolation of the limonene cyclase cDNA permits the development of an efficient expression system for this functional enzyme with which such detailed mechanistic studies can be undertaken. The limonene cyclase cDNA also provides a useful tool for isolating other monoterpene cyclase genes and for examining the developmental regulation of monoterpene biosynthesis.

In addition to the native limonene synthase amino acid sequence of SEQ ID No:11 encoded by the DNA sequence of pLC 5.2 (SEQ ID No:8), sequence variants produced by deletions, substitutions, mutations and/or insertions are intended to be within the scope of the invention except insofar as limited by the prior art.

The limonene synthase amino acid sequence variants of this invention are preferably constructed by mutating the DNA sequence that encodes wild-type limonene synthase. Generally, particular regions or sites of the DNA will be targeted for mutagenesis, and thus the general methodology employed to accomplish this is termed site-directed mutagenesis. The mutations are made using DNA modifying enzymes such as restriction endonucleases (which cleave DNA at particular locations), nucleases (which degrade DNA) and/or polymerases (which synthesize DNA).

The potential of site-directed mutagenesis to reveal active site structure-function relationships is considerable because of the power of the technique, the unique catalytic properties of the monoterpene cyclases, and the large number of mechanistic probes available from the sequences disclosed herein to examine the reaction carried out by this enzyme type. Active site cysteine and histidine residues, the conserved DDXXD motif (see SEQ ID No:11 residues 350–356), and putative deprotonation bases located by the mechanism-based inhibitor are potential targets for this approach, although other sites may be targeted using these techniques. Similarly, ongoing research with the sesquiterpene and diterpene cyclases and prenyltransferases may indicate additional conserved elements that could be targeted for mutagenesis. Photoaffinity probe techniques may also be used to locate the presumptive hydrophobic domain(s) of the monoterpene cyclases that likely will span a significant number of residues.

A His.Tag pET system (Novagen) as described below may be used for overexpression and protein purification, and can very conveniently carry out the mutagenesis studies in this expression plasmid using a two primer system such as the Transformer Site-Directed Mutagenesis kit from Clontech. Following denaturation of the target plasmid, two primers are simultaneously annealed to the plasmid; one of these primers contains the desired site-directed mutation, the other contains a mutation at another point in the plasmid resulting in elimination of a restriction site. Second strand synthesis is then carried out, tightly linking these two mutations, and the resulting plasmids are transformed into a mutS strain of *E. coli*. Plasmid DNA is isolated from the transformed bacteria, restricted with the relevant restriction enzyme (thereby linearizing the unmutated plasmids), and then retransformed into *E. coli*. This system allows for generation of mutations directly in the pET expression plasmid, without the necessity of subcloning or generation of single-stranded phagemids. The tight linkage of the two mutations and the subsequent linearization of unmutated plasmids results in high mutation efficiency and allows minimal screening. Following synthesis of the initial restriction site primer, this method requires the use of only one new primer type per mutation site. Rather than prepare each positional mutant separately, a set of "designed degenerate" oligonucleotide primers can be synthesized in order to introduce all of the desired mutations at a given site simultaneously. Transformants can be screened by sequencing the plasmid DNA through the mutagenized region to identify and sort mutant clones. Each mutant DNA can then be restricted and analyzed by electrophoresis on Mutation Detection Enhancement gel (J. T. Baker) to confirm that no other alterations in the sequence have occurred (by band shift comparison to the unmutagenized control).

In the case of the hydrophobic cleft of the cyclases, a number of residues may be mutagenized in this region. Directed mutagenesis can also be used to create cassettes for saturation mutagenesis. Once a hydrophobic segment of the active site is identified, oligonucleotide-directed mutagenesis can be used to create unique restriction sites flanking that region to allow for the removal of the cassette and the subsequent replacement with synthetic cassettes containing any number of mutations within. This approach can be carried out with any plasmid, without need for subcloning or generation of single-stranded phagemids.

The verified mutant duplexes in the pET overexpression vector can be employed to transform *E. coli* such as strain *E. coli* BL21(DE3)pLysS, for high level production of the mutant protein, and purification by metal ion affinity chromatography and thrombin proteolysis. The method of FAB-MS mapping can be employed to rapidly check the fidelity of mutant expression. This technique provides for sequencing segments throughout the whole protein and provides the necessary confidence in the sequence assignment. In a mapping experiment of this type, protein is digested with a protease (the choice will depend on the specific region to be modified since this segment is of prime interest and the remaining map should be identical to the map of unmutagenized protein). The set of cleavage fragments is fractionated by microbore BPLC (reversed phase or ion exchange, again depending on the specific region to be modified) to provide several peptides in each fraction, and the molecular weights of the peptides are determined by FAB-MS. The masses are then compared to the molecular weights of peptides expected from the digestion of the predicted sequence, and the correctness of the sequence quickly ascertained. Since this mutagenesis approach to protein modification is directed, sequencing of the altered peptide should not be necessary if the MS agrees with prediction. If necessary to verify a changed residue, CAD-tandem MS/MS can be employed to sequence the peptides of the mixture in question, or the target peptide purified for subtractive Edman degradation or carboxypeptidase Y digestion depending on the location of the modification.

In the design of a particular site directed mutagenesis, it is generally desirable to first make a non-conservative substitution (e.g., Ala for Cys, His or Glu) and determine if activity is greatly impaired as a consequence. The properties of the mutagenized protein are then examined with particular attention to the kinetic parameters of $K_m$ and $k_{cat}$ as sensitive indicators of altered function, from which changes in binding and/or catalysis per se may be deduced by comparison to the native cyclase. If the residue is by this means demonstrated to be important by activity impairment, or knockout, then conservative substitutions can be made, such as Asp for Glu to alter side chain length, Ser for Cys, or Arg for His. For hydrophobic segments, it is largely size that we will alter, although aromatics can also be substituted for alkyl side chains. The monoterpene cyclases have the intrinsic ability to construct multiple products. Thus, changes in the normal product distribution can indicate which step(s) of the reaction sequence have been altered by the mutation. For example, an increase in alcohols relative to olefins could indicate modified ionization and/or termination (solvent capture vs. deprotonation). A change in the ratio of acyclics to cyclics could implicate an alteration of the cyclization step relative to isomerization (rate data must also be considered here). Modification of the hydrophobic pocket can be employed to change binding conformations for substrate and intermediates and result in altered isomer composition reflecting regiochemical and/or stereochemical change. With an indication of the reaction step that has been compromised, other substrate and intermediate analogues and inhibitors can be employed to examine ionization, isomerization, cyclization, ion-pairing, rearrangements, termination steps and other mechanistic features of the native cyclases. Analogues can also be used to evaluate (by inhibition studies) the principal binding determinants, and any changes in binding parameters could be interpreted by this means. Equilibrium dialysis and mechanism-based inhibitors can also be used to evaluate binding phenomena in catalytically impaired mutants. For some mutants, alteration in the interaction with divalent metal ion cofactors can be revealing, as can change in pH optima that may reflect pk of active site acids or bases. These techniques can be supplemented with X-ray structural investigations, since mutagenesis alone may not distinguish between residues that are essential for catalysis and residues that are important in maintaining the overall structure of the enzyme.

Other site directed mutagenesis techniques may also be employed with the nucleotide sequences of the invention. For example, restriction endonuclease digestion of DNA followed by ligation may be used to generate deletions, as described in section 15.3 of Sambrook et al. (*Molecular Cloning: A Laboratory Manual,* 2nd Ed., Cold Spring Harbor Laboratory Press, New York, N.Y. [1989]). To use this method, it is preferable that the foreign DNA be inserted into a plasmid vector. A restriction map of both the foreign (inserted) DNA and the vector DNA must be available, or the sequence of the foreign DNA and the vector DNA must be known. The foreign DNA must have unique restriction sites that are not present in the vector. Deletions are then made in the foreign DNA by digesting it between these unique restriction sites, using the appropriate restriction endonucleases under conditions suggested by the manufacturer of the enzymes. If the restriction enzymes used create blunt ends or compatible ends, the ends can be directly ligated together using a ligase such as bacteriophage T4 DNA ligase and incubating the mixture in the presence of ATP and ligase buffer as described in section 1.68 of Sambrook et al., supra. If the ends are not compatible, they must first be made blunt by using the Klenow fragment of DNA polymerase I or bacteriophage T4 DNA polymerase, both of which require the four deoxyribonucleotide triphosphates to fill-in the overhanging single-stranded ends of the digested DNA. Alternatively, the ends may be blunted using a nuclease such as nuclease S1 or mung-bean nuclease, both of which function by cutting back the overhanging single strands of DNA. The DNA is then religated using a ligase. The resulting molecule is a limonene synthase deletion variant.

A similar strategy may be used to construct insertion variants, as described in section 15.3 of Sambrook et al., supra. After digestion of the foreign DNA at the unique restriction site(s), an oligonucleotide is ligated into the site where the foreign DNA has been cut. The oligonucleotide is designed to code for the desired amino acids to be inserted and additionally has 5' and 3' ends that are compatible with the ends of the foreign DNA that have been digested, such that direct ligation is possible.

Oligonucleotide-directed mutagenesis may be employed for preparing substitution variants of this invention. It may also be used to conveniently prepare the deletion and insertion variants of this invention. This technique is well known in the art as described by Adelman et al. (*DNA,* 2:183 [1983]). Generally, oligonucleotides of at least 25 nucleotides in length are used to insert, delete or substitute two or more nucleotides in the limonene synthase molecule. An optimal oligonucleotide will have 12 to 15 perfectly matched nucleotides on either side of the nucleotides coding for the mutation. This ensures that the oligonucleotide will hybridize properly to the single-stranded DNA template molecule. The oligonucleotides are readily synthesized using techniques well known in the art such as that described by Crea et al. (*Proc. Natl. Acad. Sci. USA,* 75:5765 [1978]), specifically incorporated by reference.

The DNA template molecule is the single-stranded form of the vector with its wild-type cDNA limonene synthase insert. The single-stranded template can only be generated by those vectors that are either derived from bacteriophage M13 vectors (the commercially available M13mp18 and M13mp19 vectors are suitable), or those vectors that contain a single-stranded phage origin of replication as described by Veira et al. (*Meth. Enzymol.,* 153:3 [1987]). Thus, the cDNA limonene synthase that is to be mutated may be inserted into one of these vectors in order to generate single-stranded template. Production of the single-stranded template is described in sections 4.21–4.41 of Sambrook et al., supra.

To mutagenize the wild-type limonene synthase, the oligonucleotide is annealed to the single-stranded DNA template molecule under suitable hybridization conditions. A DNA polymerizing enzyme, usually the Klenow fragment of *E. coli* DNA polymerase I, is then added. This enzyme uses the oligonucleotide as a primer to complete the synthesis of the mutation-bearing strand of DNA. Thus, a heteroduplex molecule is formed such that one strand of DNA encodes the wild-type limonene synthase inserted in the vector, and the second strand of DNA encodes the mutated form of limonene synthase inserted into the same vector. This heteroduplex molecule is then transformed into a suitable host cell, usually a prokaryote such as *E. coli* JM101. After growing the cells, they are plated on to agarose plates and screened using the oligonucleotide primer radiolabeled with 32-P to identify the colonies that contain the mutated limonene synthase. These colonies are selected, and the DNA is sequenced to confirm the presence of mutations in the limonene synthase molecule.

Mutants with more than one amino acid substituted may be generated in one of several ways. If the amino acids are located close together in the polypeptide chain, they may be mutated simultaneously using one oligonucleotide that codes for all of the desired amino acid substitutions. If however, the amino acids are located some distance from each other (separated by more than ten amino acids, for example) it is more difficult to generate a single oligonucleotide that encodes all of the desired changes. Instead, one of two alternative methods may be employed. In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions. The alternative method involves two or more rounds of mutagenesis to produce the desired mutant. The first round is as described for the single mutants: wild-type limonene synthase DNA is used for the template, an oligonucleotide encoding the first desired amino acid substitution(s) is annealed to this template, and the heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on.

Prokaryotes are the preferred host cells for the initial cloning steps of this invention. They are particularly useful for rapid production of large amounts of DNA, for production of single-stranded DNA templates used for site-directed mutagenesis, for screening many mutants simultaneously, and for DNA sequencing of the mutants generated. Suitable prokaryotic host cells include *E. coli* K12 strain 294 (ATCC number 31,446), *E. coli* strain W3110 (ATCC number 27,325) *E. coli* X1776 (ATCC number 31,537), and *E. coli* B; however many other strains of *E. coli*, such as HB101, JM101, NM522, NM538, NM539, and many other species and genera of prokaryotes including bacilli such as *Bacillus subtilis*, other enterobacteriaceae such as *Salmonella typhimurium* or *Serratia marcesans*, and various Pseudomonas species may all be used as hosts.

As a representative example, cDNA sequences encoding limonene synthase may be transferred to the $(His)_6$.Tag pET vector commercially available (from Novagen) for overexpression in *E. coli* as heterologous host. This pET expression plasmid has several advantages in high level heterologous expression systems. The desired cDNA insert is ligated in frame to plasmid vector sequences encoding six histidines followed by a highly specific protease recognition site (thrombin) that are joined to the amino terminus codon of the target protein. The histidine "block" of the expressed fusion protein promotes very tight binding to immobilized metal ions and permits rapid purification of the recombinant protein by immobilized metal ion affinity chromatography. The histidine leader sequence is then cleaved at the specific proteolysis site by treatment of the purified protein within thrombin, and the limonene synthase again purified by immobilized metal ion affinity chromatography, this time using a shallower imidazole gradient to elute the recombinant synthase while leaving the histidine block still adsorbed. This overexpression-purification system has high capacity, excellent resolving power and is fast, and the chance of a contaminating *E. coli* protein exhibiting similar binding behavior (before and after thrombin proteolysis) is extremely small.

The pET vector also contains a consensus ribosome binding site that directs efficient translation of the desired protein, and a strong T7 polymerase promoter to drive transcription of the cyclase gene. The T7 RNA polymerase gene is located on the bacterial host chromosome and its transcription is driven by the lacUV5 promoter (the *E. coli* host strain BL21(DE3)pLysS is also commercially available from Novagen). Upon IPTG induction, this overexpression system is capable of producing 10–90% of total *E. coli* protein as recombinant protein. In addition, the pLysS cell line maintains target genes transcriptionally silent prior to IPTG induction, allowing for expression of potentially toxic genes.

As will be apparent to those skilled in the art, other plasmid vectors containing replicon and control sequences that are derived from species compatible with the host cell may also be used in the practice of the invention. The vector usually has a replication site, marker genes that provide phenotypic selection in transformed cells, one or more promoters, and a polylinker region containing several restriction sites for insertion of foreign DNA. Plasmids typically used for transformation of *E. coli* include pBR322, pUC18, pUC19, pUCI18, pUC119, and Bluescript M13, all of which are described in sections 1.12–1.20 of Sambrook et al., supra. However, many other suitable vectors are available as well. These vectors contain genes coding for ampicillin and/or tetracycline resistance which enables cells transformed with these vectors to grow in the presence of these antibiotics.

The promoters most commonly used in prokaryotic vectors include the β-lactamase (penicillinase) and lactose promoter systems (Chang et al. *Nature*, 375:615 [1978]; Itakura et al., *Science*, 198:1056 [1977]; Goeddel et al., *Nature*, 281:544 [1979]) and a tryptophan (trp) promoter system (Goeddel et al., *Nucl. Acids Res.*, 8:4057 [1980]; EPO Appl. Publ. No. 36,776), and the alkaline phosphatase systems. While these are the most commonly used, other microbial promoters have been utilized, and details concerning their nucleotide sequences have been published, enabling a skilled worker to ligate them functionally into plasmid vectors (see Siebenlist et al., *Cell*, 20:269 [1980]).

Eukaryotic microbes such as yeasts may be used to practice this invention. The baker's yeast *Saccharomyces cerevisiae*, is a commonly used eukaryotic microorganism, although several other strains are available. The plasmid YRp7 (Stinchcomb et al., *Nature*, 282:39 [1979]; Kingsman et al., *Gene*, 7:141 [1979]; Tschemper et al., *Gene*, 10:157 [1980]) is commonly used as an expression vector in Saccharomyces. This plasmid contains the trpl gene that provides a selection marker for a mutant strain of yeast lacking the ability to grow in tryptophan, such as strains ATCC No. 44,076 and PEP4-1 (Jones, *Genetics*, 85:12 [1977]). The presence of the trpl lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman et al., *J. Biol. Chem.*, 255:2073 [1980]) or other glycolytic enzymes (Hess et al., *J. Adv. Enzyme Reg.*, 7:149 [1968]; Holland et al., *Biochemistry*, 17:4900 [1978]), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In the construction of suitable expression plasmids, the termination sequences associated with these genes are also ligated into the expression vector 3' of the sequence desired to be expressed to provide polyadenylation of the mRNA and termination. Other promoters that have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing yeast-compatible promoter, origin of replication and termination sequences is suitable.

Cell cultures derived from multicellular organisms and multicellular organisms, such as plants, may be used as hosts to practice this invention. For example, transgenic plants can be obtained such as by transferring plasmids constructed in E. coli that encode limonene synthase and preferably a selectable marker gene, e.g., the kan gene encoding resistance to kanamycin, into Agrobacterium tumifaciens containing a helper Ti plasmid as described in Hoeckema et al., Nature 303:179–181 [1983] and culturing the Agrobacterium cells with leaf slices of the plant to be transformed as described by An et al., Plant Physiology 81:301–305 [1986]. Transformed plant calli may be selected through the selectable marker by growing the cells on a medium containing, e.g., kanamycin, and appropriate amounts of phytohormone such as naphthalene acetic acid and benzyladenine for callus and shoot induction. The plant cells may then be regenerated and the resulting plants transferred to soil using techniques well known to those skilled in the art.

In addition, a gene regulating limonene synthase production can be incorporated into the plant along with a necessary promoter which is inducible. In the practice of this embodiment of the invention, the native promoter region for limonene synthase is removed from a cloned gene encoding it and is replaced with a promoter that only responds to a specific external or internal stimulus. Thus, the gene will not be transcribed except in response to the specific stimulus. As long as the gene is not being transcribed, its gene product is not produced (nor is the corresponding product, limonene).

An illustrative example of a responsive promoter system that can be used in the practice of this invention is the glutathione-S-transferase (GST) system in maize. GSTs are a family of enzymes that can detoxify a number of hydrophobic electrophilic compounds that often are used as pre-emergent herbicides (Weigand et al., Plant Molecular Biology 7:235–243 [1986]). Studies have shown that the GSTs are directly involved in causing this enhanced herbicide tolerance. This action is primarily mediated through a specific 1.1 kb mRNA transcription product. In short, maize has a naturally occurring quiescent gene already present that can respond to GSTs and that can be induced to produce a gene product. This gene has previously been identified and cloned. Thus, in one embodiment of this invention, the promoter is removed from the GST responsive gene and attached to a limonene synthase gene that previously has had its native promoter removed. This engineered gene is the combination of a promoter that responds to an external chemical stimulus and a gene responsible for successful production of limonene synthase.

In addition to the methods described above, several methods are known in the art for transferring cloned DNA into a wide variety of plant species, including gymnosperms, angiosperms, monocots and dicots (see, e.g., Glick and Thompson, eds., Methods in Plant Molecular Biology, CRC Press, Boca Raton, Fla., 1993). Representative examples include electroporation-facilitated DNA uptake by protoplasts (Rhodes et al., Science 240:(4849):204–207 [1988]); treatment of protoplasts with polyethylene glycol (Lyznik et al., Plant Molecular Biology 13:151–161 [1989]); and bombardment of cells with DNA laden microprojectiles (Klein et al., Plant Physiol. 91:440–444 [1989]) and Klein et al., Bio/Technology 6:559–563 [1988]), all incorporated by reference. Minor variations make these technologies applicable to a broad range of plant species.

Each of these techniques has advantages and disadvantages. In each of the techniques, DNA from a plasmid is genetically engineered such that it contains not only the gene of interest, but also selectable and screenable marker genes. A selectable marker gene is used to select only those cells that have integrated copies of the plasmid (the construction is such that the gene of interest and the selectable and screenable genes are transferred as a unit). The screenable gene provides another check for the successful culturing of only those cells carrying the genes of interest. A commonly used selectable marker gene is neomycin phosphotransferase II (NPT II). This gene conveys resistance to kanarnycin, a compound that can be added directly to the growth media on which the cells grow. Plant cells are normally susceptible to kanamycin and, as a result, die. The presence of the NPT II gene overcomes the effects of the kanamycin and each cell with this gene remains viable. Another selectable marker gene which can be employed in the practice of this invention is the gene which confers resistance to the herbicide glufosinate (Basta). A screenable gene commonly used is the β-glucuronidase gene (GUS). The presence of this gene is characterized using a histochemical reaction in which a sample of putatively transformed cells is treated with a GUS assay solution. After an appropriate incubation, the cells containing the GUS gene turn blue. Another screenable gene is a transcriptional activator for anthocyanin biosynthesis, as described in the copending application of Bowen et al., U.S. patent application Ser. No. 387,739, filed Aug. 1, 1989. This gene causes the synthesis of the pigment anthocyanin. Cells transformed with a plasmid containing this gene turn red. Preferably, the plasmid will contain both selectable and screenable marker genes.

The plasmid containing one or more of these genes is introduced into either maize protoplasts or callus cells by any of the previously mentioned techniques. If the marker gene is a selectable gene, only those cells that have incorporated the DNA package survive under selection with the appropriate phytotoxic agent. Once the appropriate cells are identified and propagated, plants are regenerated. Progeny from the transformed plants must be tested to insure that the DNA package has been successfully integrated into the plant genome.

Mammalian host cells may also be used in the practice of the invention. Examples of suitable mammalian cell lines include monkey kidney CVI line transformed by SV40 (COS-7, ATCC CRL 1651); human embryonic kidney line 293S (Graham et al., J. Gen. Virol. 36:59 [1977]); baby hamster kidney cells (BHK, ATCC CCL 10); Chinese hamster ovary cells (Urlab and Chasin, Proc. Natl. Acad. Sci USA, 77:4216 [1980]); mouse sertoli cells (TM4, Mather, Biol. Reprod., 23:243 [1980]); monkey kidney cells (CVI-76, ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442; human lung cells (W138, ATCC CCL 75); human liver cells (Hep G2, HB 8065); mouse mammary tumor cells (MMT 060562, ATCC CCL 51); rat hepatoma cells (HTC, MI.54, Baumann et al., J. Cell Biol., 85:1 [1980]); and TRI cells (Mather et al., Annals N.Y. Acad. Sci., 383:44 [1982]). Expression vectors for these cells ordinarily include (if necessary) DNA sequences for an origin of replication, a promoter located in front of the gene to be expressed, a ribosome binding site, an RNA splice site, a polyadenylation site, and a transcription terminator site.

Promoters used in mammalian expression vectors are often of viral origin. These viral promoters are commonly derived from polyoma virus, Adenovirus2, and most frequently Simian Virus 40 (SV40). The SV40 virus contains two promoters that are termed the early and late promoters. These promoters are particularly useful because they are both easily obtained from the virus as one DNA fragment that also contains the viral origin of replication (Fiers et al., Nature, 273:113 [1978]). Smaller or larger SV40 DNA fragments may also used, provided they contain the approximately 250-bp sequence extending from the HindIII site toward the BglI site located in the viral origin of replication.

Alternatively, promoters that are naturally associated with the foreign gene (homologous promoters) may be used provided that they are compatible with the host cell line selected for transformation.

An origin of replication may be obtained from an exogenous source, such as SV40 or other virus (e.g., Polyoma, Adeno, VSV, BPV) and inserted into the cloning vector. Alternatively, the origin of replication may be provided by the host cell chromosomal replication mechanism. If the vector containing the foreign gene is integrated into the host cell chromosome, the latter is often sufficient.

Satisfactory amounts of limonene synthase are produced by transformed cell cultures. However, the use of a secondary DNA coding sequence can enhance production levels. The secondary coding sequence typically comprises the enzyme dihydrofolate reductase (DHFR). The wild-type form of DHFR is normally inhibited by the chemical methotrexate (MTX). The level of DHFR expression in a cell will vary depending on the amount of MTX added to the cultured host cells. An additional feature of DHFR that makes it particularly useful as a secondary sequence is that it can be used as a selection marker to identify transformed cells. Two forms of DHFR are available for use as secondary sequences, wild-type DHFR and MTX-resistant DHFR. The type of DHFR used in a particular host cell depends on whether the host cell is DHFR deficient (such that it either produces very low levels of DHFR endogenously, or it does not produce functional DHFR at all). DHFR-deficient cell lines such as the CHO cell line described by Urlaub and Chasin, supra, are transformed with wild-type DHFR coding sequences. After transformation, these DHFR-deficient cell lines express functional DHFR and are capable of growing in a culture medium lacking the nutrients hypoxanthine, glycine and thymidine. Nontransformed cells will not survive in this medium.

The MTX-resistant form of DHFR can be used as a means of selecting for transformed host cells in those host cells that endogenously produce normal amounts of functional DHFR that is MTX sensitive. The CHO-Kl cell line (ATCC number CL 61) possesses these characteristics, and is thus a useful cell line for this purpose. The addition of MTX to the cell culture medium will permit only those cells transformed with the DNA encoding the MTX-resistant DHFR to grow. The nontransformed cells will be unable to survive in this medium.

Many eukaryotic proteins normally secreted from the cell contain an endogenous signal sequence as part of the amino acid sequence. This sequence targets the protein for export from the cell via the endoplasmic reticulum and Golgi apparatus. The signal sequence is typically located at the amino terminus of the protein, and ranges in length from about 13 to about 36 amino acids. Although the actual sequence varies among proteins, all known eukaryotic signal sequences contain at least one positively charged residue and a highly hydrophobic stretch of 10–15 amino acids (usually rich in the amino acids leucine, isoleucine, alanine, valine and phenylalanine) near the center of the signal sequence. The signal sequence is normally absent from the secreted form of the protein, as it is cleaved by a signal peptidase located on the endoplasmic reticulum during translocation of the protein into the endoplasmic reticulum. The protein with its signal sequence still attached is often referred to as the 'pre-protein' or the immature form of the protein.

However, not all secreted proteins contain an amino terminal signal sequence that is cleaved. Some proteins, such as ovalbumin, contain a signal sequence that is located on an internal region of the protein. This sequence is not normally cleaved during translocation.

Proteins normally found in the cytoplasm can be targeted for secretion by linking a signal sequence to the protein. This is readily accomplished by ligating DNA encoding a signal sequence to the 5' end of the DNA encoding the protein and then expressing this fusion protein in an appropriate host cell. The DNA encoding the signal sequence may be obtained as a restriction fragment from any gene encoding a protein with a signal sequence. Thus, prokaryotic, yeast, and eukaryotic signal sequences may be used herein, depending on the type of host cell utilized to practice the invention. The DNA encoding the signal sequence portion of the gene is excised using appropriate restriction endonucleases and then ligated to the DNA encoding the protein to be secreted, i.e. limonene synthase.

Selection of a functional signal sequence requires that the signal sequence is recognized by the host cell signal peptidase such that cleavage of that signal sequence and secretion of the protein will occur. The DNA and amino acid sequence encoding the signal sequence portion of several eukaryotic genes including, for example, human growth hormone, proinsulin, and proalbumin are known (see Stryer, Biochemistry, W. H. Freeman and Company, New York, N.Y., p. 769, [1988]) and can be used as signal sequences in appropriate eukaryotic host cells.

Yeast signal sequences, as for example acid phosphatase (Arima et al., Nuc. Acids Res., 11:1657 [1983]), alpha-factor, alkaline phosphatase and invertase may be used to direct secretion from yeast host cells. Prokaryotic signal sequences from genes encoding, for example, LamB or OmpF (Wong et al., Gene 68:193 [1988]), MalE, PhoA, or beta-lactamase, as well as other genes, may be used to target proteins from prokaryotic cells into the culture medium.

As described above, the limonene synthase amino terminal transit peptide resides at SEQ ID No:11, residues 1 through 89, and in the embodiment shown in SEQ ID No:11 directs the enzyme to plastids for processing to the mature protein. Alternative transit sequences from plants, animals and microbes can be employed in the practice of the invention to direct the gene product to the cytoplasm, endothelial reticulum, mitochondria or other cellular components, or to target the protein for export to the medium. These considerations apply to the overexpression of limonene synthase or limonene, and to direction of expression within an intact organism to permit gene product function in any desired location.

An alternative technique to provide a protein of interest with a signal sequence such that it may be secreted is to chemically synthesize the DNA encoding the signal sequence. In this method, both strands of an oligonucleotide encoding the selected signal sequence are chemically synthesized and then annealed to each other to form a duplex. The double-stranded oligonucleotide is then ligated to the 5' end of the DNA encoding the protein.

The construct containing the DNA encoding the protein with the signal sequence ligated to it can then be ligated into a suitable expression vector. This expression vector is transformed into an appropriate host cell and the protein of interest is expressed and secreted.

Transformation of cultured plant host cells is normally accomplished through Agrobacterium tumifaciens, as described above. Cultures of mammalian host cells and other host cells that do not have rigid cell membrane barriers are usually transformed using the calcium phosphate method as originally described by Graham and Van der Eb (*Virology,* 52:546 [1978]) and modified as described in sections 16.32–16.37 of Sambrook et al. supra. However, other methods for introducing DNA into cells such as Polybrene (Kawai and Nishizawa, *Mol. Cell. Biol.,* 4:1172 [1984]), protoplast fusion (Schaffner, *Proc. Natl. Acad. Sci. USA,* 77:2163 [1980]), electroporation (Neumann et al., *EMBO J.,* 1:841 [1982]), and direct microinjection into nuclei (Capecchi, *Cell,* 22:479 [1980]) may also be used.

Yeast host cells are generally transformed using the polyethylene glycol method, as described by Hinnen (*Proc. Natl. Acad. Sci. U.S.A.,* 75:1929 [1978]).

Prokaryotic host cells or other host cells with rigid cell walls are preferably transformed using the calcium chloride method as described in section 1.82 of Sambrook et al., supra. Alternatively, electroporation may be used for transformation of these cells.

Construction of suitable vectors containing DNA encoding replication sequences, regulatory sequences, phenotypic selection genes and the limonene synthase DNA of interest are prepared using standard recombinant DNA procedures. Isolated plasmids and DNA fragments are cleaved, tailored, and ligated together in a specific order to generate the desired vectors.

The DNA is cleaved using the appropriate restriction enzyme or enzymes in a suitable buffer. (Appropriate buffers, DNA concentrations, and incubation times and temperatures are specified by the manufacturers of the restriction enzymes). After incubation, the enzymes and other contaminants are removed by extraction of the digestion solution with a mixture of phenol and chloroform, and the DNA is recovered from the aqueous fraction by precipitation with ethanol.

To ligate the DNA fragments together to form a functional vector, the ends of the DNA fragments must be compatible with each other. In some cases the ends will be directly compatible after endonuclease digestion. However, it may be necessary to first convert the sticky ends, commonly produced by endonuclease digestion, to blunt ends to make them compatible for ligation. It is then purified by phenolchloroform extraction and ethanol precipitation.

The cleaved DNA fragments may be size-separated and selected using DNA gel electrophoresis. The DNA may be electrophoresed through either an agarose or a polyacrylamide matrix. The selection of the matrix will depend on the size of the DNA fragments to be separated. After electrophoresis, the DNA is extracted from the matrix by electroelution, or, if low-melting agarose has been used as the matrix, by melting the agarose and extracting the DNA from it, as described in sections 6.30–6.33 of Sambrook et al., supra.

The DNA fragments that are to be ligated together (previously digested with the appropriate restriction enzymes such that the ends of each fragment to be ligated are compatible) are present in solution in about equimolar amounts. The solution will also contain ATP, ligase buffer and a ligase such as T4 DNA ligase. If the DNA fragment is to be ligated into a vector, the vector is first linearized by cutting with the appropriate restriction endonuclease(s) and then phosphatased with either bacterial alkaline phosphatase or calf intestinal alkaline phosphatase. This prevents self-ligation of the vector during the ligation step.

After ligation, the vector with the foreign gene now inserted is transformed into a suitable host cell, most commonly a prokaryote such as *E. coli* K12 strain 294 (ATCC number 31,446) or another suitable *E. coli* strain. The transformed cells are selected by growth on an antibiotic, commonly kanamycin (kan), tetracycline (tet) or ampicillin (amp), to which they are rendered resistant due to the presence of kan, tet and/or amp resistance genes on the vector. If the ligation mixture has been transformed into a eukaryotic mammalian host cell, transformed cells may be selected by the DHFR/MTX system described above. The transformed cells are grown in culture and the plasmid DNA (plasmid refers to the vector ligated to the foreign gene of interest) is then isolated. This plasmid DNA is then analyzed by restriction mapping and/or DNA sequencing. DNA sequencing is generally performed by either the method of Messing et al., *Nucleic Acids Res.,* 9:309 (1981) or by the method of Maxam et al., *Methods of Enzymology,* 65:499 (1980).

After mammalian host cells have been stably transformed with the DNA, the DHFR-protein-coding sequences are amplified by growing the host cell cultures in the presence of methotrexate. The effective range of concentrations of MTX is highly dependent upon the nature of the DHFR gene and protein and the characteristics of the host. Clearly, generally defined upper and lower limits cannot be ascertained. Suitable concentrations of other folic acid analogs or other compounds that inhibit DHFR may also be used. MTX itself is, however, convenient, readily available, and effective.

As discussed above, limonene synthase variants are preferably produced by means of mutation(s) that are generated using the method of site-specific mutagenesis. This method requires the synthesis and use of specific oligonucleotides that encode both the sequence of the desired mutation and a sufficient number of adjacent nucleotides to allow the oligonucleotide to stably hybridize to the DNA template.

The foregoing may be more fully understood in connection with the following representative examples, in which "Plasmids" are designated by a lower case p followed by an alphanumeric designation. The starting plasmids used in this invention are either commercially available, publicly available on an unrestricted basis, or can be constructed from such available plasmids using published procedures. In addition, other equivalent plasmids are known in the art and will be apparent to the ordinary artisan.

"Digestion", "cutting" or "cleaving" of DNA refers to catalytic cleavage of the DNA with an enzyme that acts only at particular locations in the DNA. These enzymes are called restriction endonucleases, and the site along the DNA sequence where each enzyme cleaves is called a restriction site. The restriction enzymes used in this invention are commercially available and are used according to the instructions supplied by the manufacturers. Restriction enzymes are designated by abbreviations composed of a capital letter followed by two or three lower case letters representing the microorganism from which each restriction enzyme was obtained. These letters are followed by one or more Roman numerals that identify the particular enzyme. In general, about 1 $\mu$g of plasmid or DNA fragment is used with about 2 units of enzyme in about 20 $\mu$l of buffer solution. The appropriate buffer, substrate concentration, incubation temperature, and incubation time for each enzyme is specified by the manufacturer. After incubation, the enzyme and other contaminants are removed from the DNA by extraction with a solution of phenol-chloroform, and the digested DNA is recovered from the aqueous fraction by precipitation with ethanol. Digestion with a restriction enzyme may be followed by treatment with bacterial alkaline phosphatase or calf intestinal alkaline phosphatase. This prevents the two restriction cleaved ends of a DNA fragment from "circularizing" or forming a closed loop that would impede insertion of another DNA fragment at the restriction site. Unless otherwise stated, digestion of plasmids is not followed by 5' terminal dephosphorylation. These procedures and reagents for dephosphorylation are described in sections 1.60–1.61 and sections 3.38–3.39 of Sambrook et al., supra.

"Recovery" or "isolation" of a given fragment of DNA from a restriction digest means separation of the resulting DNA fragment on a polyacrylamide or an agarose gel by electrophoresis, identification of the fragment of interest by comparison of its mobility versus that of marker DNA fragments of known molecular weight, removal of the gel section containing the desired fragment, and separation of the gel from: DNA. This procedure is known generally. For example, see Lawn et al. (*Nucleic Acids Res.* 9:6103–6114 [1982]), and Goeddel et al. (*Nucleic Acids Res.*, supra).

"Southern Analysis" is a method by which the presence of DNA sequences in a digest or DNA-containing composition is confirmed by hybridization to a known, labeled oligonucleotide or DNA fragment. Southern analysis refers to the separation of digested DNA on an agarose gel, denaturation of the DNA, and transfer of the DNA from the gel to a nitrocellulose or nylon membrane using methods originally described by Southern (*J. Mol. Biol.*, 98:503 [1975]) and modified as described in sections 9.31–9.57 of Sambrook et al., supra.

"Transformation" means introducing DNA into an organism so that the DNA is replicable, either as an extrachromosomal element or chromosomal integrant. The method used for transformation depends on whether the host cell is a eukaryote or a prokaryote. The method used to transform prokaryotes is the calcium chloride method as described in section 1.82 of Sambrook et al., supra. Eukaryotes are transformed using the calcium phosphate method as described in sections 16.32–16.37 of Sambrook et al., supra.

"Ligation" refers to the process of forming phosphodiester bonds between two double stranded DNA fragments using the enzyme ligase in a suitable buffer that also contains ATP.

"Oligonucleotide" refers to short length single or double stranded sequences of deoxyribonucleotides linked via phosphodiester bonds. The oligonucleotides are chemically synthesized by known methods and purified on polyacrylamide gels.

The following examples merely illustrate the best mode now contemplated for practicing the invention, but should not be construed to limit the invention. All literature citations herein are expressly incorporated by reference.

EXAMPLES

Example 1

Plant Material and Limonene Synthase Isolation

Plant materials—Spearmint (*Mentha spicata* L.) plants were propagated from rhizomes or stem cuttings in peat moss:pumice:sand (58:35:10, v/v/v) and were grown in a greenhouse with supplemental lighting (16 h, 21,000 lux minimum) and a 30°/15° C. (day/night) temperature cycle. Plants were watered as needed and fertilized daily with a complete fertilizer (N:P:K, 20:20:20) plus iron chelate and micronutrients. Apical buds and newly emerged, rapidly-expanding leaves (5–10 mm long) of vegetative stems (3–7 weeks old) were used for nucleic acid isolation and for the preparation of glandular trichome cells for enzyme extraction. [1-$^3$H]Geranyl pyrophosphate (120 Ci/mol) was prepared by NaB$^3$H$_4$ (Du Pont/NEN) reduction of geranial, followed by pyrophosphorylation and separation of the resulting products according to the procedure of Croteau and Karp, *Arch. Biochem. Biophys.* 176:734–746 [1976]. Final purification was achieved by anion-exchange chromatography of a DEAE-cellulose column eluted with a linear gradient (10–80 mM) of (NH$_4$)$_2$CO$_3$, pH 9.0. The product gave a single band (Rf=0.4) by TLC on buffered silica gel G (100 mM (NH$_4$)$_2$SO$_4$, pH 9.0) developed with n-propanol:conc. NH$_4$OH:H$_2$O (6:3:1, v/v/v).

Limonene synthase isolation—Limonene synthase was extracted from a purified preparation of glandular trichome secretory cell clusters. To obtain these clusters, plant material was soaked in ice-cold, distilled water for 1 h and gently abraded in a cell disrupter (Bead-Beater, Bio-Spec Products, Bartlesville, Okla.). Batches of 20 g of plant material were abraded in the 300 ml polycarbonate chamber of the cell disrupter with 130 g glass beads (0.5 mm diameter, Bio-Spec Products), 20 g Amberlite XAD-4 resin and buffer (25 mM Hepes, pH 7.3, containing 200 mM sorbitol, 0.8% (w/v) methyl cellulose, 10 mM sucrose, 10 mM KCl, 5 mM MgCl$_2$, 0.5 mM potassium phosphate and 1% (w/v) polyvinylpyrrolidone, M$_r$=40,000) added to full volume. Larger batches of plant material were abraded in 600 ml chambers of our own manufacture that had relative proportions similar to the 300 ml chamber. Removal of glandular trichome secretory cells was accomplished by three 1 min pulses of operation with the rotor speed controlled by a rheostat set at 90 V. This procedure was carried out at 4° C., and after each pulse the chamber was allowed to cool for 1 min. The isolated secretory cell clusters were separated from the glass beads, XAD-4 resin and residual plant material by sieving through a series of nylon meshes. The secretory cell clusters (approximately 60 $\mu$m in diameter) readily passed through meshes of 350 and 105 $\mu$m and were collected on a mesh of 20 $\mu$m. After filtration, cell clusters were suspended in the cell disruption buffer and allowed to settle for 30 min at 4° C., after which the upper few ml of buffer, containing non-glandular trichomes and other low-density matter were discarded.

Suspensions of isolated secretory cell clusters (3 to 5×10$^5$ clusters/ml) were disrupted by sonication with a microprobe (Braun-Sonic 2000) at maximum power for two 1-min bursts. Sonication was carried out in a buffer of 25 mM potassium phosphate, pH 6.0, containing 25% (v/v) XAD-4 resin. After sonication, the resulting extract was filtered through 20 $\mu$m nylon mesh, and the filtrate centrifuged at 16,000 g for 15 min (pellet discarded) and again at 195,000 g for 90 min to provide the soluble supernatant used as the enzyme source. This crude enzyme solution could be stored at −20° C. for two months without significant loss of activity.

Example 2

Limonene Synthase Purification

All procedures were carried out at 0°–4° C. The 195,000 g supernatant from Example 1 was dialyzed against 25 mM Mes buffer, pH 6.1, containing 10% (w/v) glycerol and 1 mM dithiothreitol, and, after being adjusted to 20 mM MgCl$_2$, was desalted (Econo-Pac 10DG desalting column, Bio-Rad) into 30 mM Mes buffer, pH 6.1, containing 10%

(v/v) glycerol, 100 mM KCl and 0.5 mM dithiothreitol, and then applied to a DEAE-Sepharose Fast Flow anion-exchange column (10×100 mm; Pharmacia FPLC System). Proteins were eluted with a 24 ml linear gradient from 100 to 500 mM KCl in the loading buffer. The limonene synthase activity eluted as a single peak between 300–340 mM KCl. The eluate was subjected to dye-ligand chromatography on a 3 ml column of Matrex Gel Red A (3 mg dye/ml, Amicon) pre-equilibrated with the same buffer containing 20 $MgCl_2$. The column was washed with 50 ml of the equilibration buffer to remove unbound proteins, and the limonene synthase activity was then eluted with 20 ml of 100 mM potassium phosphate, pH 7.6, containing 10% (v/v) glycerol and 0.5 mM dithiothreitol. The purity of the protein was judged to be ~99% by SDS-PAGE (Laemmli, *Nature* 227:680–685 [1970]) with silver staining (Wray et al., *Anal. Biochem.* 118:197–203 [1981]).

The eluate from anion-exchange chromatography was mixed with an equal volume of 100 mM potassium phosphate buffer, pH 7.0, containing 2M $(NH_4)_2SO_4$, 5% (v/v) glycerol and 0.5 mM dithiothreitol, and subjected to hydrophobic interaction chromatography (HIC) on an HRLC MP7 HIC column ($C_1$ ligand, Bio-Rad), pre-equilibrated with 100 mM potassium phosphate buffer, pH 7.0, containing 1M $(NH_4)_2SO_4$, 5% (w/v) glycerol and 0.5 mM dithiothreitol. The column was developed with a 10 ml reversed gradient from 1.0 to 0.0M $(NH_4)_2SO_4$ (1 ml fractions, 1 ml/min) in the same buffer. The purified limonene synthase activity eluted in a single peak (2 ml) between 300–100 mM $(NH_4)_2SO_4$.

To obtain sufficient quantities of enzyme product for characterization, limonene synthase was partially purified by subjecting the 195,000 g supernatant to anion-exchange chromatography on 20 g of DEAE-cellulose (DE-52, Whatman). The column was equilibrated with 15 mM sodium phosphate buffer, pH 6.0, containing 1 mM sodium ascorbate, 0.5 mM dithiothreitol and 0.2 mM EDTA. After the 195,000 g supernatant was loaded, the column was washed with 100 ml equilibration buffer containing 100 mM NaCl, and the limonene synthase activity then eluted with 100 ml of the same buffer containing 250 mM NaCl. Following anion-exchange chromatography on DEAE-cellulose, the limonene synthase appeared to represent 40% of the total protein as judged by SDS-PAGE (data not shown).

Gel electrophoresis—SDS-PAGE was carried out according to Laemmli (*Nature*, supra) in 10% polyacrylamide vertical slab gels (16 cm×18 cm×1 mm, Hoefer SE600 vertical gel apparatus). Aliquots of the purified limonene synthase from above (~50 µg) were dialyzed against water, lyophilized, resuspended in SDS sample buffer (Laemmli et al., *Nature*, supra) and denatured on a steam bath for 5 min before loading. Gels were run at a constant current of 20 mA for about 3 h, and were stained with 0.25% (w/v) Coomassie Brilliant Blue R-250 in methanol:acetic acid:$H_2O$ (30:10:60) and destained in methanol:acetic acid:$H_2O$ (35:10:55). Some gels were also silver stained (Wray et al., *Anal. Biochem.* 118:197–203 [1981]). Molecular weight markers were obtained from Diversified Biotech.

For nondenaturing PAGE, a 10% polyacrylamide vertical slab gel (16 cm×18 cm×1 mm) employing a discontinuous buffer system (Jouin, *Biochemistry* 12:871–879 [1973]) without SDS was cast and subjected to pre-electrophoresis for 30 min at 20 mA in buffer containing 1 mM sodium thioglycolate to remove residual persulfate used in polymerization (Moos et al., *J. Biol. Chem.* 263:6005–6008 [1988]). Protein samples were dialyzed against 62 mM Tris-HCl buffer, pH 6.6, containing 5 mM dithiothreitol and 10% (w/v) glycerol, and aliquots containing 100–300 µg protein were loaded into 1 cm-wide wells and electrophoresed at a constant voltage of 25 V for 20 h at 4° C. Limonene synthase activity was localized by assay of gel slices (0.8 cm) in 1.0 ml of assay buffer (see below); this activity migrated with an $R_m$=0.82.

Example 3

Limonene Synthase Activity Assay

The reaction was initiated by addition of 10 µM (1-$^3$H) geranyl pyrophosphate. Pentane (1 ml) was carefully layered on top of the aqueous assay mixture to trap volatile products. After incubation for 1 h at 30° C. with gentle agitation, the reaction was stopped by chilling and vigorous mixing, NaCl was added to saturation, and the assay tube was centrifuged to separate the phases. The pentane layer was removed, the aqueous phase reextracted with an additional 1 ml of pentane, and the combined pentane extract was passed over a short column of silica gel (SilicAR 60 A. Mallinckrodt) overlaid with $MgSO_4$ in a Pasteur pipet. This procedure affords an extract containing only hydrocarbons, such as limonene, and is free of oxygenated products which remain adsorbed to the silica gel. When an evaluation of the full range of metabolites produced in the assay was required (i.e., including oxygenated products, such as geraniol, liberated from the substrate by endogenous phosphohydrolases), the remaining aqueous phase was also extracted with diethyl ether and the ether passed through the original silica gel column to recover the oxygenated products. Radioactivity in the pentane and diethyl ether eluates was determined by liquid scintillation counting in 10 ml of cocktail containing 0.4% (w/v) Omnifluor (Du Pont) dissolved in 30% ethanol in toluene, using a Packard Tricarb 460 CD liquid scintillation spectrometer ($^3$H efficiency= 42%). For product identification by GLC or radio-GLC, aliquots of the assay extracts were diluted with the appropriate internal standards and concentrated under a stream of $N_2$. Preparative incubations, used to generate product for subsequent characterization, were carried out in a slightly modified assay buffer of 10 mM Mopso-5 mM sodium phosphate, pH 7.0, containing 10% (w/v) glycerol, 1 mM sodium ascorbate, 1 mM $MnCl_2$ and 0.5 mM dithiothreitol. Protein concentrations were estimated by the dye-binding technique of Bradford (*Anal. Biochem.* 72:248–254 [1976]) using the Bio-Rad protein assay kit with lysozyme as standard. Both enzyme activity measurements and protein determinations were reproducible to within 10%.

Example 4

Amino Acid Analysis and Protein Sequencing

Approximately 25 µg of purified limonene synthase was subjected to acid hydrolysis and subsequent amino acid analysis at the Washington State University Bioanalytical Center. In preparation for proteolysis and peptide sequencing, approximately 75 µg of purified protein was subjected to SDS-PAGE according to the method of Schagger and von Jagow (Schagger and von Jagow, *Anal. Biochem.* 166:368–379 [1987]) in 10% polyacrylamide vertical slab gels (16 cm×18 cm×0.7 mm). Gels were stained with Coomassie Brilliant Blue R-250 in methanol:acetic acid:water (30:10:60, v/v/v) and destained (in methanol:acetic acid: :water (10:10:80 v/v/v) and the gel bands containing the limonene synthase (at 56 kD) were excised, washed with water, incubated in SDS sample buffer (Laemmli, supra) for 30 min at 30° C., and then inserted into the sample wells of a 16.5% polyacrylamide vertical slab gel (16 cm×18 cm×1.0 mm) for SDS-PAGE as before (Schagger and von Jagow, supra). Each gel slice was overlaid with buffer consisting of 0.125M Tris (pH 6.8), 1 mM EDTA, 2.5 mM dithiothreitol and 0.1% (v/v) SDS and containing 2 μg V8 protease (Sigma) according to the standard practice (Cleveland et al., J. Biol. Chem. 252:1102–1106 [1977]). Samples were electrophoresed until the bromophenol blue dye had traveled about 1 cm to concentrate the protein into the stacking gel, and the power was turned off for 50 min to permit proteolytic digestion. Electrophoresis was then continued for 20 h at a constant voltage of 90v.

For sequence analysis, polyvinylidenedifluoride membranes (Immobilon-$P^{SQ}$, Millipore) were first wetted in methanol and equilibrated in 25 mM Tris-190 mM glycine (pH 8.3) containing 20% (v/v) methanol and then gel blotted in the same buffer (Towbin et al., Proc. Natl. Acad. Sci. USA 76:4350–4354 [1979]). Electroblotting was carried out for 90 min at a constant current of 100 mA using a Hoefer TE 70 semi-dry transfer apparatus. Peptides were sequenced via Edman degradation on an Applied Biosystems 470 sequenator at the Washington State University Laboratory for Bioanalysis and Biotechnology.

For CNBr cleavage, approximately 50 μg of purified limonene synthase was lyophilized in a 1.5 ml microfuge tube and dissolved in 200 μl of a degassed solution containing 10 μg/μl CNBr in 70% aqueous formic acid. After thorough mixing and flushing with Ar, the mixture was incubated in the dark for 20 h at 20° C. The sample was dried and excess CNBr and formic acid removed under vacuum (Savant Speed Vac), and the wall of the tube was washed down with 200 μl 0.001N $nH_4OH$ and the sample redried under vacuum. The sample was then resuspended in SDS buffer (Laemmli, supra) and subjected to SDS-PAGE as before (Schagger and von Jagow, supra) in 16.5% polyacrylamide vertical slab gels (16 cm×18 cm×1.0 mm), electroblotted to polyvinylidenedifluoride (Immobilon $P^{SQ}$), and the peptides subjected to Edman degradative sequencing as described above for peptides generated by V8 proteolysis. Alternatively, the CNBr-generated peptides were dissolved in 10% aqueous acetonitrile with 0.1% (v/v) trifluoroacetic acid (starting solvent) and separated by reversed phase HPLC (Rainin, C4-Dynamax 300A column) with a linear gradient from starting solvent to 80% aqueous acetonitrile with 0.07% trifluoroacetic acid. Purified peptides in the lyophilized chromatographic fractions were sequenced as above.

Example 5

Plasmid Formation and Screening

Isolation of nucleic acids—Newly emerging spearmint leaves with a very high density of developing epidermal oil glands were used as starting material. Total RNA (yield ~1 mg/g fr. tissue wt.) was extracted using the procedures of Cathala and associates (Cathala et al., DNA 2:329–335 [1983]), with the substitution of 300 mM for 50 mM Tris in the tissue homogenization buffer. Poly(A)$^+$ RNA was purified by chromatography on an oligo(dT)-cellulose column (Pharmacia). Plasmid DNA was amplified in Escherichia coli strain XL1-Blue and was prepared by standard procedures (Sambrook et al., supra).

Library construction and screening—A spearmint leaf cDNA library was constructed from 5 μg poly(A)$^+$ mRNA using the ZAP-cDNA synthesis kit with lambda UniZap XR vector, and was packaged using the Gigapack II Packaging Extract according to the manufacturer's instructions (Stratagene). Using the sequence information obtained from peptides generated by CNBr cleavage and V8 proteolysis of limonene synthase, three degenerate oligonucleotide probes were synthesized (at the Washington State University Laboratory for Bioanalysis and Biotechnology) (see FIG. 2) and end labeled with $^{32}$P using T4 kinase (Bethesda Research Laboratories) by standard procedures (Titus, Promega Protocols and Applications Guide, 2nd Ed., Promega Corp., Madison, Wis., [1991]). The three probes were used to screen replicate filter lifts of 2.5×10$^5$ primary plaques grown in E. coli PLK-F' using the Stratagene protocols. The hybridization conditions were modified from the NEN procedure using 6×SSC (1×SSC=0.15M NaCl in 0.015M sodium citrate, pH 7.0) containing 1% SDS, 10% dextran sulfate, and 50 μg/ml each of salmon sperm and E. coli DNA at 47° C. for 20 h. Blots were washed twice in 6×SSC for 5 min at 47° C., thrice in 3×SSC for 30 min, dried in a vacuum oven and, as in all instances described here where $^{32}$P-labeled probes were used, autoradiograms were prepared with Kodak XAR-5 film exposed overnight at –80° C. Plaques affording positive signals with each of the three probes (a total of 20 were picked) were rescreened on E. coli XL1-Blue through four cycles using each probe individually until clones pLC 4.1, pLC 5.2, pLC 8.5 and pLC 10.1, that hybridized to all three probes, were pure. The selected lambda UniZap XR clones were in vivo excised and recircularized as Bluescript II SK(+) phagemids that were then employed to infect E. coli XL1-Blue using procedures provided by Stratagene.

Example 6 cDNA Expression

Expression of limonene synthase cDNA—E. coli XL1-Blue cells containing Bluescript II SK(+), pLC 4.1, pLC 5.2, pLC 8.5 or pLC 10.1 were grown to stationary phase in 5 mls Luria-Bertani medium with 100 μg/ml ampicillin and used to inoculate 100 ml liquid cultures either without or with 50 μg/ml antibiotic which were incubated at 37° C. with shaking at 350 rpm. When the cultures reached $A_{600}$=0.5, either 1 mM or 10 mM IPTG was added to induce the cultures which were incubated for an additional 2 h. Cells were collected by centrifugation at 2400 g for 10 min, resuspended in 20 mM Tris (pH 7.5) and centrifuged again, then suspended in 2.5 mL buffer containing 20 mM Mopso (pH 7.0), 1 mM EDTA, 1 mM dithiothreitol and 10% (v/v) glycerol and disrupted by sonication (Braun-Sonic 2000 with microprobe at maximum power for four 1-min bursts at 0°–4° C.). The bacterial homogenates were then clarified by centrifugation at 13,000 g (the pellets contained negligible limonene cyclase activity), the resulting supernatants dialyzed to standard assay conditions, and the assay for limonene cyclase activity carried out under linear conditions as described above (Alonso et al., J. Biol. Chem., supra). In some instances, portions of these preparations were taken for immunoblotting (described below) or were partially purified by anion exchange chromatography. In the latter case, the supernatant was desalted into 15 mM potassium phosphate buffer (pH 6.0) containing 10% (v/v) glycerol, 150 mM KCl and 1 mM dithiothreitol, and then applied to a DEAE-Sepharose Fast Flow column (5×100 mm, Pharmacia FPLC system) that was eluted with a linear gradient from 150 to 600 mM KCl in loading buffer. This limonene cyclase activity expressed in E. coli eluted as a single peak between 365 and 465 mM KCl, as with the native enzyme from Mentha.

To examine the possible production of limonene in transformed E. coli, cultures harboring pLC 5.2 (showing the highest limonene synthase specific activity by in vitro assay) were grown as before to various densities corresponding to $A_{600}$=0.3 to 0.8. IPTG (10 mM) was added and the induced cultures were incubated for an additional 1–2 h to provide enzyme activity levels ranging from 10 to 50 nmol/h/culture; in some instances, a pentane overlay (10 ml/culture) was added to trap the volatile olefinic product. Following incubation, the cultures were chilled in ice, saturated with NaCl, homogenized and extracted with pentane (3×10 ml), and the combined pentane extract was passed over a silica gel column to provide the hydrocarbon fraction, free of oxygenated metabolites. The internal standard was added (10 nmol p-cymene) and the solvent concentrated under a stream of $N_2$ in preparation for analysis of the hydrocarbon fraction by capillary GLC.

Example 7

Cloning in pET Vector

Cloning into the pET vector requires two unique restriction sites in the target gene: a NdeI site overlapping the translation initiation codon and a BamHI site at the 3' end. The latter site is easily engineered through cloning, in the correct orientation, into the polylinker region of pBluescript SK II (Stratagene) in which the gene at this stage will residue. The NdeI site can be engineered through use of PCR. In the case of the (−)-limonene synthase cDNA (nascent protein), there is an additional NdeI site within the 3'-untranslated sequence. In order to remove this NdeI site, add an NdeI site at the initiation codon, and position a BamHI site at the 3' end of the clone, the following strategy was employed to express the limonene synthase preprotein. The entire coding region of the pLC 5.2 cDNA was amplified by PCR using two primers: one primer was positioned downstream of the coding region but upstream of the existing NdeI site; the other primer corresponded to sixteen nucleotides of a KpnI/NdeI linker overlapping with the first twenty nucleotides of the pLC 5.2 coding region. The amplified product was blunted at both ends, using the Klenow fragment of DNA polymerase I, then digested with KpnI in order to create a sticky end for directional cloning. This product was then cloned into pBluescript SK II digested with KpnI and SmaI. The resulting plasmid contained the entire pLC 5.2 coding region with the requisite NdeI and BamHI restriction sites. After limited sequencing to confirm that no errors were introduced by PCR, the pLC 5.2 coding region was excised with NdeI and BamHI and cloned directly into the corresponding sites of the His.Tag pET vector.

The verified plasmid was used to transform the E. coli BL21(DE3)pLysS strain and, following induction, growth at room temperature, harvest and purification by metal ion affinity chromatography/thrombin proteolysis, gave ~15% yield of the recombinant nascent limonene synthase as total cellular protein. Little proteolysis of the nascent synthase transit peptide was observed in E. coli BL21(DE3) strain in vivo, perhaps because of strain differences (BL21 is deficient in several major proteases), the fact that the preprotein arises as the $(His)_6$-fusion protein, or that protein synthesis simply "out-runs" proteolysis in this system.

Example 8

Limonene Synthase Analysis

Product analysis and other analytical methods—Radio-GLC was performed on a Gow-Mac 550P gas chromatograph attached to a Packard 894 gas proportional counter (Satterwhite and Croteau, *J. Chromatogr.* 452:61–73 [1987]) under conditions designed to separate limonene from all other naturally occurring monoterpene olefins (Rajaonarivony et al., *Arch. Biochem. Biophys.*, supra).

Capillary GLC was utilized for the analysis of limonene production by transformed E. coli cultures (Hewlett-Packard 5890: injector, 220° C.; detector, 300° C.; split ratio, 5:1; $H_2$ carrier at 14 psi. column: 0.25 mm i.d.×30 m with 0.25 μm film of AT-1000 (Alltech); programmed from 35° C. (5 min) to 230° C. at 10° C./min). Based on internal standardization with p-cymene, and the detector response, an amount of limonene equivalent to 0.5 nmol per culture can be easily determined by this method.

Procedures for immunoblotting on nitrocellulose using polyclonal antibodies generated in rabbits against spearmint limonene synthase, and detection by alkaline phosphatase conjugated goat anti-rabbit IgG, have been described (Alonso et al., *Arch. Biochem. Biophys.*, supra). Cross-reacting antibodies to E. coli proteins were removed by subjecting the antiserum to affinity chromatography using a column of soluble proteins from XL-1 Blue/Bluescript II SK(+) linked to CNBr-activated Sepharose (Sigma) following established protocols (Harlow and Lane, *Antibodies: A Laboratory Manual*, Cold Spring Harbor Laboratory, Cold Spring Harbor, N.Y. [1988]). In some instances, horseradish peroxidase conjugated goat anti-rabbit IgG (1:2,000; Bio-Rad Laboratories) was substituted as the secondary antibody, and positives were detected by enhanced chemiluminescence on Kodak XAR-5 film after treating the filters with the Amersham enhancing reagents. For quantitation, blots were scanned at 633 nm with an LKB 2202 Ultroscan laser densitometer. In most instances, ~100 μg of E. coli protein was employed and was dialyzed against 20 mM Tris (pH 6.8) containing 1 mM dithiothreitol and 10% (v/v) glycerol, lyophilized, and thermally denatured in the presence of SDS and β-mercaptoethanol (Laemmli, supra) before use. Protein concentrations were estimated by dye-binding using the Bio-Rad Protein Assay, and Rainbow molecular weight markers for use in blotting were obtained from Amersham.

For RNA blot analysis, spearmint and peppermint poly $(A)^+$ RNA (3 μg each) were separated on a 1.5% formaldehyde agarose gel and blotted onto Genescreen Plus nylon membranes (NEN). Probe DNA was prepared by digesting pLC 5.2 with SmaI and ApaI, separated by agarose gel electrophoresis, and electroeluted using standard procedures (Titus, supra). The cDNA insert was then labeled with $^{32}P$ via the hexamer reaction (Cathala et al., supra). Hybridization according to the NEN protocol was for 16 h at 42° C. in 15 mls of hybridization solution consisting of 5×SSPE (1×SSPE=150 mM NaCl, 10 mM sodium phosphate and 1 mM EDTA), 50% deionized formamide, 5×Denhardts, 1% SDS, and 100 μg/ml denatured, sheared salmon sperm DNA. Blots were washed twice for 5 min with SSPE at room temperature, thrice at 65° C. for 45 min with 2×SSPE containing 2% SDS, and finally thrice for 15 min with 0.1×SSPE at room temperature.

Sequencing double-stranded phagemid DNA of pLC 5.2 and the other clones was by chain termination method using Sequenase Version 2.0 (United States Biochemical). Both strands of the pLC 5.2 cDNA were completely sequenced using T7 and T3 primers with additional primers synthesized as needed. DNA fragments were assembled and the sequence analyzed using SEQAID II. version 3.81 (a public domain program provided by the authors D. D. Rhodes and D. J. Roufa, Kansas State University), and the Genetics Computer Group Packet (Devereaux et al., supra). The sequence of the positive coding strand is set forth in SEQ ID No:8 and shown in FIG. 4.

While the preferred embodiment of the invention has been illustrated and described, it will be appreciated that various changes can be made therein without departing from the spirit and scope of the invention. For example, sequence variations from those described and claimed herein as deletions, substitutions, mutations, insertions and the like are intended to be within the scope of the claims except insofar as limited by the prior art.

The embodiments of the invention in which an exclusive property or privilege is claimed are defined as follows:

1. An isolated nucleotide sequence encoding limonene synthase.

2. A nucleotide sequence of claim 1 encoding limonene synthase from *Mentha spicata*.

3. An isolated nucleotide sequence encoding a protein having the biological activity of SEQ ID No:11.

4. The isolated nucleotide sequence of claim 3 which encodes the amino acid sequence of SEQ ID No:11.

5. The isolated nucleotide sequence of claim 3 having the sequence of SEQ ID No:8.

6. A replicable expression vector comprising a nucleotide sequence encoding a protein having the biological activity of SEQ ID No:11.

7. The replicable expression vector of claim 6 wherein the nucleotide sequence comprises the sequence of SEQ ID No:8.

8. A host cell comprising a vector of claim 6.

9. A host cell comprising a vector of claim 7.

10. A method of enhancing the production of limonene synthase in a suitable host cell comprising introducing into the host cell an expression vector of claim 6 under conditions enabling expression of the protein in the host cell.

* * * * *

UNITED STATES PATENT AND TRADEMARK OFFICE
CERTIFICATE OF CORRECTION

PATENT NO. : 5,871,988
DATED : February 16, 1999
INVENTOR(S) : R.B. Croteau et al.

It is certified that error appears in the above-identified patent and that said Letters Patent is hereby corrected as shown below:

On the title page,

| | | |
|---|---|---|
| [75] Pg. 1, col. 1 | Inventors | "Shelia" should read --Sheila-- |
| Column | Line | |
| 1 | 53 | "Harbome" should read --Harborne-- |
| 11 | 50 | "His.Tag" should read --His•Tag-- |
| 12 | 42 | "BPLC" should read --HPLC-- |
| 15 | 35 | "(His)$_6$.Tag" should read --(His)$_6$•Tag-- |
| 18 | 11 | "kanarnycin" should read --kanamycin-- |
| 29 | 49 | "His.Tag" should read --His•Tag-- |

Signed and Sealed this

Eleventh Day of April, 2000

Attest:

Attesting Officer

Q. TODD DICKINSON

Director of Patents and Trademarks